(12) United States Patent
Tang et al.

(10) Patent No.: US 11,396,528 B2
(45) Date of Patent: Jul. 26, 2022

(54) POLYPEPTIDE AND USE THEREOF

(71) Applicant: BGI SHENZHEN, Shenzhen (CN)

(72) Inventors: Yunxia Tang, Shenzhen (CN); Bo Li, Shenzhen (CN); Yong Hou, Shenzhen (CN); Shuntao Luo, Shenzhen (CN); Ying Huang, Shenzhen (CN); Geng Liu, Shenzhen (CN); Dongli Li, Shenzhen (CN); Xiumei Lin, Shenzhen (CN)

(73) Assignee: BGI SHENZHEN, Shenzhen (CN)

(*) Notice: Subject to any disclaimer, the term of this patent is extended or adjusted under 35 U.S.C. 154(b) by 361 days.

(21) Appl. No.: 16/417,564

(22) Filed: May 20, 2019

(65) Prior Publication Data
US 2019/0270775 A1    Sep. 5, 2019

Related U.S. Application Data

(63) Continuation of application No. PCT/CN2016/107751, filed on Nov. 29, 2016.

(51) Int. Cl.
| | |
|---|---|
| *C07K 7/06* | (2006.01) |
| *A61P 35/00* | (2006.01) |
| *A61K 35/17* | (2015.01) |
| *A61K 38/08* | (2019.01) |
| *A61K 39/00* | (2006.01) |
| *G01N 33/574* | (2006.01) |
| *C12N 15/52* | (2006.01) |
| *C07K 16/00* | (2006.01) |
| *C12N 9/00* | (2006.01) |
| *C12N 15/63* | (2006.01) |

(52) U.S. Cl.
CPC .............. *C07K 7/06* (2013.01); *A61K 35/17* (2013.01); *A61K 38/08* (2013.01); *A61K 39/0011* (2013.01); *A61K 39/001154* (2018.08); *A61P 35/00* (2018.01); *C07K 16/00* (2013.01); *C12N 9/00* (2013.01); *C12N 15/52* (2013.01); *C12N 15/63* (2013.01); *G01N 33/57415* (2013.01); *A61K 2039/55566* (2013.01); *A61K 2039/6006* (2013.01)

(58) Field of Classification Search
None
See application file for complete search history.

(56) References Cited

U.S. PATENT DOCUMENTS 7,504,490 B1 * 3/2009 Weinstock .............. C07K 14/38
435/252.3
2019/0309019 A1 * 10/2019 Tang .................. A61K 39/0011

FOREIGN PATENT DOCUMENTS

| CN | 102459314 | 5/2012 | |
|---|---|---|---|
| WO | 2015161274 | 10/2015 | |
| WO | WO-2016187508 A2 * | 11/2016 | ..... A61K 39/001164 |

OTHER PUBLICATIONS

WIPO, ISR for PCT/CN2016/107751, dated Aug. 25, 2017.

* cited by examiner

*Primary Examiner* — Peter J Reddig
(74) *Attorney, Agent, or Firm* — Hodgson Russ LLP

(57) ABSTRACT

Provided are a polypeptide and nucleic acid for encoding the polypeptide, a nucleic-acid construct, an expression vector, and a host cell containing the nucleic acid, an antigen-presenting cell presenting the polypeptide on the surface of the cell, and immune effector cell thereof, a pharmaceutical composition containing the polypeptide, a vaccine containing the nucleic acid, the nucleic acid construct, the expression vector, the host cell, the antigen-presenting cell, and the immune effector cell, and an antibody recognizing the polypeptide. Also provided is a therapeutic method using the polypeptide, the nucleic acid, the pharmaceutical composition, the vaccine, and the antibody. Also provided are a diagnosis method and diagnosis apparatus for detecting the described polypeptide. Also provided is an application of the polypeptide in preparing a vaccine, a tumor diagnosis kit, or a pharmaceutical composition, and an application of the polypeptide or the nucleic acid as a test target in tumor diagnosis.

14 Claims, 6 Drawing Sheets

Specification includes a Sequence Listing.

POLYPEPTIDE AND USE THEREOF

CROSS-REFERENCE TO RELATED APPLICATIONS

This application is a continuation of International Application No. PCT/CN2016/107751, filed Nov. 29, 2016, the entire disclosure of which is incorporated herein by reference.

FIELD

The present disclosure relates to the field of biomedicine, in particular to a polypeptide and use thereof; more particular to a polypeptide and use thereof in the preparation of a kit, a medicament and a vaccine, and to the use thereof in preventing or treating a disease associated with a mutation of PIK3CA gene in a subject; to a nucleic acid, a nucleic acid construct, an expression vector, a host cell, a pharmaceutical composition, an antigen-presenting cell, an immune effector cell, a vaccine, an antibody; and to a therapeutic method, a diagnostic method and a diagnostic system.

BACKGROUND

Cancer is a disease involving abnormal cell proliferation due to genetic mutation in cells, which has become one of major threats and a main cause to human health. In the Global Cancer Report 2014 distributed by the World Health Organization (WHO), it is indicated that the number of global cancer patients and cancer deaths are in a rapid increase in 2012, and nearly half of the newly-diagnosed patients are Asian populations, especially from China (which ranks the first in newly-diagnosed cancer cases). It is also showed by data in the China Cancer Registry Annual Report 2012 that the number of annual newly-diagnosed cancer patients is about 3.5 million, and 2.5 million patients of which even progress to death. Thus, it has an important clinical value to discover an effective and specific cancer therapy.

Traditional tumor therapies mainly include surgery, radiotherapy and chemotherapy, however all of them have great limitations. For example, a high tumor metastasis recurrence rate after surgical resection is mainly due to proximal invasion or distant metastasis of cancer cells, and radiotherapy and chemotherapy will cause severe damage to normal cells in the body, especially to the hematopoietic system and immune system, thus it is difficult to achieve a better long-term curative effect for patients with tumor metastasis. With an in-depth study of the molecular mechanism of tumor and the development of biotechnology, targeted therapy (which mainly involves monoclonal antibody classified as a passive immunotherapy sometimes, and small molecule targeted drugs) and immunotherapy (which mainly includes cytokine therapy, immune checkpoint inhibitor, adoptive cell transfer, tumor vaccine and the like) are increasingly playing an important role in the integrated tumor treatment, in which immunotherapy enhances anti-tumor immunity in a tumor microenvironment by regulating the immune system of the body, thereby inhibiting and killing tumor cells in a highly effective and specific way with good tolerance, thus it has a wide prospect in tumor therapy.

Tumor immunotherapeutic vaccines mainly include tumor cell vaccine, dendritic cell (DC cell) vaccine, protein & polypeptide vaccine, nucleic acid vaccine and genetic engineering vaccine, which will kill tumors mainly by mechanisms of inducing an immune response by the tumor-specific as antigen in a patient, including an antigen-antibody reaction and specific killing of cytotoxic T lymphocyte (CTL) which plays a vital role in the tumor immune response. A tumor-specific polypeptide, as a tumor-specific antigen which will induce specific CTL killing, includes tumor-mutant polypeptides and tumor-specific overexpressed polypeptides. The tumor-mutant polypeptide, which is only presented in tumor of a patient, is a specific target of tumor immunotherapy, with good safety and low side effect. The immunotherapy targeting the tumor-mutant polypeptide is represented by polypeptide-specific DC-CTL and adoptive transfer of tumor infiltrating lymphocytes (TIL), and exhibits a good therapeutic effect.

The tumor-specific polypeptides can be recognized by CTL cells or TIL cells under the presentation of human leukocyte antigen (HLA). The HLAs are divided into two classes (HLA-I and HLA-II), where the HLA-I class includes three subtypes HLA-A, HLA-B and HLA-C and each of them can also have several subtypes depending on different sequences, for example, one of subtype HLA-As is HLA-A0201, which is in a high percent (accounting for 13%) in Chinese populations. Different polypeptides have different binding activity to HLA-A0201. In tumor patients having specific HLA subtypes, only a portion of mutant polypeptides can be bond to corresponding HLAs and followed by presented to CTL cells or TIL cells via HLAs depending on the HLA subtypes.

However, there still remains a need to further research and develop the tumor immunotherapy.

SUMMARY

Embodiments of the present disclosure seek to solve at least one of the problems existing in the related art to at least some extent.

In one aspect of the present disclosure, provided in embodiments is an isolated polypeptide of SEQ ID NO: 1 (GLKDLLNPI) or a fragment thereof. According to embodiments of the present disclosure, the fragment comprises at least 9 amino acids which has at least 70%, at least 75%, at least 80%, at least 85%, at least 90%, at least 95%, or at least 99% sequence identity to the isolated polypeptide of SEQ ID NO: 1, or has one or more of amino acid substitution(s), deletion(s) and addition(s) compared to the isolated polypeptide of SEQ ID NO: 1.

In one embodiment of the present disclosure, the one or more of amino acid substitution(s), deletion(s) and/or addition(s) is at least one of amino acid substitution at position 2 and amino acid substitution at position 9 in the amino acid sequence as depicted in SEQ ID NO: 1.

In one embodiment of the present disclosure, the one or more of amino acid substitution(s), deletion(s) and/or addition(s) is at least one of substitution with Methionine at position 2 and substitution with Leucine at position 9 in the amino acid sequence as depicted in SEQ ID NO: 1.

In one embodiment of the present disclosure, the fragment has 9 amino acids as depicted in any one of SEQ ID NO: 1, SEQ ID NO: 2, SEQ ID NO: 3 and SEQ ID NO: 4.

```
                                          (SEQ ID NO: 1)
GLKDLLNPI.

(SEQ ID NO: 2)
GLKDLLNPL.
```

-continued

GMKDLLNPL. (SEQ ID NO: 3)

GMKDLLNPI. (SEQ ID NO: 4)

In embodiments of the present disclosure, the polypeptide binds with high affinity to HLA-A0201, thus having the ability to activate specific T cell immunity.

In another aspect of the present disclosure, provided in embodiments is use of a reagent for detecting the polypeptide as described above in the preparation of a kit for diagnosing a tumor. Optionally, the polypeptide is expressed in a tumor from a HLA-A0201 positive subject. Optionally, the tumor is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor. Preferably, the tumor is breast cancer. Based on the experiments and investigations, it is found by the present inventors that the polypeptide as described above is specifically overexpressed in a tumors. Further, it is verified through experiments and proposed by the present inventors that the kit prepared with the reagent for detecting the polypeptide as described above can be useful in diagnosing a tumor effectively. Meanwhile, it is surprisingly discovered by the present inventors that the polypeptide binds with high affinity to HLA-A0201 and thus can be presented by HLA-A0201-expressing presenting cells to CTL cells or TIL cells for activation of specific T cell immunity, therefore when the polypeptide is expressed in a tumor from a HLA-A0201 positive subject, the safety and effectiveness of diagnosis by the kit can be significantly improved. Further, it is also discovered by the present inventors that the polypeptide is specifically overexpressed in a tumor selected from one or more of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor, especially breast cancer, thus when the tumor as described above is diagnosed, the effectiveness and sensitivity of diagnosis by the kit can be further improved.

In another aspect of the present disclosure, provided in embodiments is use of the polypeptide as described above in the preparation of a medicament for preventing or treating a tumor. Optionally, the polypeptide is expressed in a tumor from a HLA-A0201 positive subject. Optionally, the tumor is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor. Preferably, the tumor is breast cancer. As described above, it is found by the present inventors that the polypeptide as described above is specifically overexpressed in a tumor. Further, it is verified through experiments and proposed by the present inventors that the medicament prepared with the polypeptide as described above can be useful in effectively preventing or treating a tumor. It is found that when the polypeptide is expressed in a tumor from a HLA-A0201 positive subject, the safety and effectiveness of the treatment or prevention by the medicament are significantly improved. Furthermore, if the tumor is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor, especially breast cancer, the effectiveness and sensitivity of the treatment or prevention by the medicament can be further improved.

In another aspect of the present disclosure, provided in embodiments is an isolated nucleic acid.

According to an embodiment of the present disclosure, the isolated nucleic acid is a nucleic acid encoding the polypeptide or the fragment thereof as described above or a complement thereof, wherein the isolated nucleic acid is capable of specifically encoding the polypeptide. As described above, the polypeptide binds with high affinity to HLA-A0201 and thus can be presented by HLA-A0201-expressing presenting cells to CTL cells or TIL cells for activation of specific T cell immunity. Therefore, the polypeptide expressed by the isolated nucleic acid proposed in embodiments of the present disclosure under a suitable condition can be used to prevent or treat a tumor, especially the polypeptide-expressing tumor from the HLA-A0201 positive subject, the safety and effectiveness of the treatment or prevention are improved.

In another aspect of the present disclosure, provided in embodiments is a nucleic acid construct.

According to an embodiment of the present disclosure, the nucleic acid construct includes an encoding sequence, wherein the encoding sequence is the nucleic acid as described above, and optionally a control sequence operably connected to the encoding sequence, wherein the control sequence is one or more control sequence(s) capable of directing the expression of the polypeptide in a host cell. Therefore, after transfected or infected under a suitable condition with the nucleic acid construct proposed in embodiments of the present disclosure which is connected with a vector, the suitable host cell can express the polypeptide as described above, thus being capable of specifically preventing or treating a tumor in an effective way, particularly the polypeptide-expressing tumor from the HLA-A0201 positive subject.

In another aspect of the present disclosure, provided in embodiments is an expression vector.

According to an embodiment of the present disclosure, the expression vector includes the nucleic acid construct as described above. Therefore, after transfected or infected with the expression vector in embodiments of the present disclosure under a suitable condition, the host cell can efficiently express the polypeptide as described above, thus being capable of specifically preventing or treating a tumor in an effective way, particularly the polypeptide-expressing tumor from the HLA-A0201 positive subject.

In another aspect of the present disclosure, provided in embodiments is a host cell.

According to an embodiment of the present disclosure, the host cell carries the nucleic acid construct or the expression vector as described above, optionally obtained by transfecting or transforming the nucleic acid construct or the expression vector. According to an embodiment of the present disclosure, the host cell can efficiently express the polypeptide as described above under a suitable condition, thus being capable of specifically preventing or treating a tumor in an effective way, particularly the polypeptide-expressing tumor from the HLA-A0201 positive subject.

In another aspect of the present disclosure, provided in embodiments is a pharmaceutical composition.

According to an embodiment of the present disclosure, the pharmaceutical composition includes the polypeptide as described above, and a pharmaceutically acceptable adjuvant. It is discovered by the present inventors through a lot of experiments that the pharmaceutical composition including the polypeptide as described above and the pharmaceutically acceptable adjuvant can significantly stimulate the proliferation and secretion of CTL cells or TIL cells, remarkably killing the tumor cell which expresses the polypeptide as an antigen, thus exhibiting an efficacy of significantly preventing or treating a tumor, particularly the tumor specifically overexpressing the polypeptide as an antigen.

In another aspect of the present disclosure, provided in embodiments is use of the polypeptide as described above in the preparation of a vaccine for preventing or treating a tumor. Optionally, the polypeptide is expressed in a tumor from a HLA-A0201 positive subject. Optionally, the tumor is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor. Preferably, the tumor is breast cancer. As described above, it is found by the present inventors that the polypeptide as described above is specifically overexpressed in a tumor. Further, it is verified through experiments and proposed by the present inventors that the vaccine prepared with the polypeptide as described above can be useful in effectively preventing or treating a tumor, with higher safety and lower side effect. It is found that when the polypeptide is expressed in a tumor from a HLA-A0201 positive subject, the safety and effectiveness of the treatment or prevention by the vaccine are significantly improved. Furthermore, if the tumor is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor, especially breast cancer, the effectiveness and sensitivity of the treatment or prevention by the vaccine can be further improved.

In another aspect of the present disclosure, provided in embodiments is an antigen-presenting cell.

According to an embodiment of the present disclosure, the antigen-presenting cell presents the polypeptide as described above. According to an embodiment of the present disclosure, the antigen-presenting cell which presents the polypeptide described above can effectively induce an immune response by the tumor-specific polypeptide as described above (as antigen) in a subject, thus activating the function of specific CTL killing. The antigen-presenting cell proposed in embodiments of the present disclosure has a significant efficacy of treating the polypeptide-expressing tumor from the HLA-A0201 positive subject with higher safety.

In another aspect of the present disclosure, provided in embodiments is an immune effector cell.

According to an embodiment of the present disclosure, the immune effector cell can recognize the polypeptide as described above or the antigen-presenting cell presenting the polypeptide as described above on its surface. According to an embodiment of the present disclosure, the immune effector cell specifically kills the polypeptide-expressing tumor from the HLA-A0201 positive subject.

In another aspect of the present disclosure, provided in embodiments is a vaccine.

According to an embodiment of the present disclosure, the vaccine includes the nucleic acid, the nucleic acid construct, the expression vector, the host cell, the antigen-presenting cell, or the immune effector cell as described above. As mentioned above, after transfected or infected with the nucleic acid, the nucleic acid construct or the expression vector proposed in embodiments of the present disclosure under a suitable condition, the host cell can express the polypeptide as described above, thus the nucleic acid, the nucleic acid construct and the expression vector in embodiments of the present disclosure each can be used for preventing or treating the polypeptide-expressing tumor; further the antigen-presenting cell proposed in embodiments of the present disclosure has a significant efficacy in treating the polypeptide-expressing tumor from the HLA-A0201 positive subject; and furthermore the immune effector cell proposed in embodiments of the present disclosure has a significant efficacy in specifically killing a target cell expressing the polypeptide as an antigen. The vaccine proposed in embodiments of the present disclosure has a significant efficacy of preventing or treating the polypeptide-expressing tumor from the HLA-A0201 positive subject with higher safety and lower side effect.

In another aspect of the present disclosure, provided in embodiments is an antibody.

According to an embodiment of the present disclosure, the antibody specifically recognizes the polypeptide as described above. The antibody proposed in embodiments of the present disclosure can specifically bind to said polypeptide, thereby being capable of specifically identifying a tumor cell which specifically overexpresses the polypeptide, thus the antibody proposed in the embodiment of the present disclosure plays a huge role in tumor diagnosis, treatment or prevention.

In another aspect of the present disclosure, provided in embodiments is a therapeutic method.

According to embodiments of the present disclosure, the therapeutic method includes administering to a subject a therapeutically effective amount of the polypeptide, the nucleic acid, the nucleic acid construct, the expression vector, the host cell, the pharmaceutical composition, the antigen-presenting cell, the immune effector cell, the vaccine or the antibody as described above. As mentioned above, the therapeutic method proposed in embodiments of the present disclosure including administering a therapeutically effective amount of any of the polypeptide, the nucleic acid, the nucleic acid construct, the expression vector, the host cell, the pharmaceutical composition, the antigen-presenting cell, the immune effector cell, the vaccine and the antibody as described above is capable of effectively treating or preventing the polypeptide-expressing tumor from the HLA-A0201 positive subject.

In another aspect of the present disclosure, provided in embodiments is use of the polypeptide as described above in the prevention or treatment of a disease associated with a mutation of PIK3CA gene in a subject. The polypeptide in embodiments of the present disclosure useful in preventing or treating a disease associated with a mutation of PIK3CA gene in a subject exhibits a significant efficacy.

In another aspect of the present disclosure, provided in embodiments is a diagnostic method.

According to an embodiment of the present disclosure, the diagnostic method includes: detecting whether a biological sample derived from a subject contains the polypeptide or the fragment thereof as described above, and determining whether the subject suffers from a tumor based on the presence or absence of the polypeptide in the biological sample, optionally the polypeptide is expressed in a tumor from a HLA-A0201 positive subject, and optionally the tumor is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor. Preferably, the tumor is breast cancer. It is found by the present inventors that the polypeptide is specifically overexpressed in a tumor, whereas such the polypeptide is absent in a tumor-free tissue, thus a subject with a tumor specifically overexpressing the polypeptide can be effectively diagnosed by the diagnostic method proposed in embodiments of the present disclosure. It is further discovered by the present inventors that the polypeptide is specifically overexpressed in a tumor selected from one or more of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor, thus the accuracy of diagnosing the tumor as described above can be further improved by using the diagnostic method proposed in the embodiment of the present disclosure. Meanwhile, it is demonstrated by the present inventors that HLA-A0201 is present in Chinese populations in a high proportion, which binds with strong affinity to the polypeptide for activation of a serious of immune responses, thus the accuracy of diagnosis of the polypeptide-expressing tumor from the HLA-A0201 positive subject is improved by using the diagnostic method proposed in the embodiment of the present disclosure.

In another aspect of the present disclosure, provided in embodiments is a diagnostic system.

According to an embodiment of the present disclosure, the diagnostic system includes a polypeptide detecting device, configured to detect whether a biological sample derived from a subject contains the polypeptide as described above; and a diagnosis determining device, connected to the polypeptide determining device and configured to determine whether the subject suffers from a tumor based on the presence or absence of the polypeptide in the biological sample.

In an embodiment of the present disclosure, the polypeptide is expressed in a tumor from a HLA-A0201 positive subject.

In an embodiment of the present disclosure, the tumor described in this aspect is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor. Preferably, the tumor is breast cancer. It is found by the present inventors that the polypeptide is specifically overexpressed in a tumor, whereas such the polypeptide is absent in a tumor-free tissue, thus a subject with a tumor specifically overexpressing the polypeptide can be effectively diagnosed by the diagnostic system proposed in embodiments of the present disclosure. It is further discovered by the present inventors that the polypeptide is specifically overexpressed in a tumor selected from one or more of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor, especially breast cancer, thus the accuracy of diagnosing the tumor as described above can be further improved by using the diagnostic system proposed in the embodiment of the present disclosure. Meanwhile, it is demonstrated by the present inventors that HLA-A0201 is present in Chinese populations in a high proportion, which binds with strong affinity to the polypeptide for activation of a serious of immune responses, thus the accuracy of diagnosis of the polypeptide-expressing tumor from the HLA-A0201 positive subject is improved by using the diagnostic system proposed in the embodiment of the present disclosure.

The additional aspects and advantages of the present disclosure will be partly described below, which will be apparent from the part description or be understood by the practice of the present disclosure.

BRIEF DESCRIPTION OF THE DRAWINGS

The above and/or additional aspects and advantages of the present disclosure will become apparent and readily understood from the description of examples of the present disclosure in combination with the following drawings.

where panel A shows inhibition of tumor growth after treatment of an adjuvant alone group, an adjuvant+wild-type polypeptide (depicted in GLEDLLNPI, SEQ ID NO: 5) group, an adjuvant+mutant polypeptide (depicted in GLKDLLNPI, SEQ ID NO:1), an adjuvant+mutant polypeptide's variant (depicted in GLKDLLNPL, SEQ ID NO:2) group, an adjuvant+mutant polypeptide's variant (depicted in GMKDLLNPL, SEQ ID NO:3) group and an adjuvant+mutant polypeptide's variant (depicted in GMKDLLNPI, SEQ ID NO:4) group, respectively, panel B shows a mouse survival rate after treatment of an adjuvant alone group, an adjuvant+wild-type polypeptide (depicted in GLEDLLNPI, SEQ ID NO: 5) group, an adjuvant+mutant polypeptide (depicted in GLKDLLNPI, SEQ ID NO:1), an adjuvant+mutant polypeptide's variant (depicted in GLKDLLNPL, SEQ ID NO:2) group, an adjuvant+mutant polypeptide's variant (depicted in GMKDLLNPL, SEQ ID NO:3) group and an adjuvant+mutant polypeptide's variant (depicted in GMKDLLNPI, SEQ ID NO:4) group, respectively

DETAILED DESCRIPTION

Figure 1:
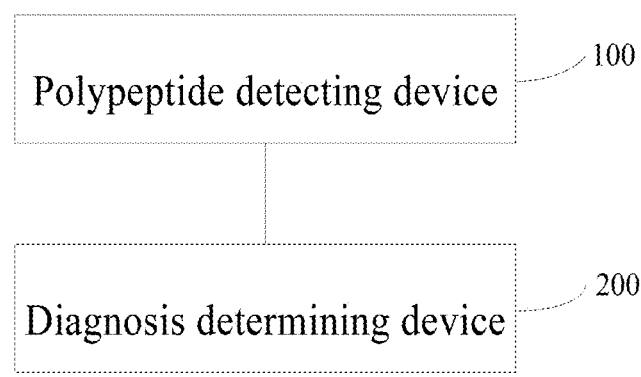
FIG. 1 is a schematic block diagram showing a diagnostic system according to an embodiment of the present disclosure.

The embodiments of the present disclosure are described in detail below with reference to the drawings, and the same or similar elements and the elements having identical or similar functions are denoted by like reference numerals throughout the descriptions. The embodiments described herein with reference to drawings are explanatory, illustrative, and used to generally understand the present disclosure. The embodiments shall not be construed to limit the present disclosure.

It should be noted that the terms "first" and "second" are used herein for purposes of description and are not intended to indicate or imply relative importance or significance, impliedly indicate the quantity of the technical feature referred to. Thus, the features defined with "first" and "second" may explicitly or impliedly comprise one or more such features. In the description of the present disclosure, "a plurality of" means two or more than two this features, unless specified otherwise.

Polypeptide

In a first aspect of the present disclosure, provided in embodiments is an isolated polypeptide of SEQ ID NO: 1 (GLKDLLNPI) or a fragment thereof. According to embodiments of the present disclosure, the fragment comprises at least 9 amino acids which has at least 70%, at least 75%, at least 80%, at least 85%, at least 90%, at least 95%, or at least 99% sequence identity to the isolated polypeptide of SEQ ID NO: 1, or has one or more of amino acid substitution(s), deletion(s) and addition(s) compared to the isolated polypeptide of SEQ ID NO: 1.

The polypeptide proposed in embodiments of the present disclosure is derived from a mutant polypeptide in a tumor which is only present in a tumor from a subject with mutation and is absent in a tumor-free tissue, thus exhibiting high specificity, and activating an immune response with high specificity. The CTLs produced in body by stimulation of the polypeptide proposed in embodiments of the present disclosure kill tumor cells and tissues only, which do not affect normal tissues, thereby achieving accurate targeted therapy to tumor. Using the polypeptide proposed in embodiments of the present disclosure for tumor immunotherapy achieves not only a good therapeutic effect, but also good safety and low side effect.

Particularly, according to an embodiment of the present disclosure, the one or more of amino acid substitution(s), deletion(s) and/or addition(s) as described above is at least one of amino acid substitution(s) at position 2 and amino acid substitution at position 9 in the amino acid sequence as depicted in SEQ ID NO: 1. It is found by the present inventors that the amino acid substitutions at position 2 and/or position 9 as depicted in SEQ ID NO: 1 does not change the specificity between the substituted amino acids and T cells, thus the immunogenicity of polypeptides is not changed.

More particularly, according to an embodiment of the present disclosure, the one or more of amino acid substitution(s), deletion(s) and/or addition(s) as described above is at least one of substitution with Methionine at position 2 and substitution with Leucine at position 9 in the amino acid sequence as depicted in SEQ ID NO: 1. For example, the fragment has 9 amino acids as depicted in any one of SEQ ID NO:1, SEQ ID NO: 2, SEQ ID NO: 3 and SEQ ID NO: 4.

According to an embodiment of the present disclosure, the polypeptides depicted in GLKDLLNPI (SEQ ID NO: 1), GLKDLLNPL (SEQ ID NO: 2), GMKDLLNPL (SEQ ID NO: 3) and GMKDLLNPI (SEQ ID NO: 4) each bind to HLA-A0201 with a high affinity, thus having the ability to activate specific T cell immunity. It is further discovered by the present inventors that the variants depicted in GLKDLLNPL (SEQ ID NO: 2), GMKDLLNPL (SEQ ID NO: 3) and GMKDLLNPI (SEQ ID NO: 4), where the amino acid at position 2 is substituted with Methionine and/or the amino acid at position 9 is substituted with Leucine, have an enhanced affinity with HLA-A0201, without affecting the specificity between the polypeptides and T cells, and thus the immunogenicity of polypeptides is not changed. Therefore, the polypeptides depicted in both SEQ ID NO: 1 and SEQ ID NOs: 2-4 each have the ability to activate specific T cell immunity.

Usage

In terms of application, in one aspect of the present disclosure, provided in embodiments is use of a reagent for detecting the polypeptide as described above in the preparation of a kit for diagnosing a tumor, use of the polypeptide as described above in the preparation of a medicament for preventing or treating a tumor, or use of the polypeptide as described above in the preparation of a vaccine for preventing or treating a tumor. Optionally, the polypeptide is expressed in a tumor from a HLA-A0201 positive subject. Optionally, the tumor is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor. Preferably, the tumor is breast cancer. Based on the experiments and investigations, it is found by the present inventors that the polypeptide as described above is specifically overexpressed in a tumor. Further, it is verified through experiments and proposed by the present inventors that the kit prepared with the reagent for detecting the polypeptide as described above, or the medicament and the vaccine prepared with the polypeptide as described above, can be useful in diagnosing a tumor effectively, with higher safety and lower side effect. Meanwhile, it is surprisingly discovered by the present inventors that the polypeptide binds with high affinity to HLA-A0201, and thus can be presented by HLA-A0201-expressing presenting cells to CTL cells or TIL cells for activation of specific T cell immunity, therefore when the polypeptide is expressed in a tumor from a HLA-A0201 positive subject, the safety and effectiveness of diagnosis by the kit or of treatment by the medicament or vaccine can be significantly improved. Further, it is also discovered by the present inventors that the polypeptide is specifically overexpressed in a tumor selected from one or more of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia and brain tumor, especially breast cancer, thus when the tumor as described above is diagnosed or treated, the effectiveness of diagnosis by the kit or of treatment by the medicament or vaccine can be further improved.

In another aspect of the present disclosure, provided in embodiments is use of the polypeptide as described above in the prevention or treatment of a disease associated with a mutation of PIK3CA gene in a subject. With a lot of screening experiments, it is found by the present inventors that the mutation occurring in the wild-type PIK3CA gene causes the amino acid encoded at position 453 to be mutated into Lysine (i.e. Lys or K) from Glutamic acid (i.e. Glu or E). The polypeptides in embodiments of the present disclosure have same antigenic property as the polypeptide encoded by the mutated PIK3CA gene, which cause specific immune response and allow the effector cells generated to specifically recognize and kill PIK3CA gene-mutated cells significantly, thus being capable of preventing or treating diseases associated with PIK3CA gene mutation. Also it is demonstrated by the present inventors through experiments that the polypeptides in embodiments of the present disclosure can prevent or treat diseases associated with PIK3CA gene mutation, with significant efficacy.

Therapeutic Composition

In another aspect of the present disclosure, provided in embodiments is an isolated nucleic acid. According to an embodiment of the present disclosure, the isolated nucleic acid is a nucleic acid encoding the polypeptide or the fragment thereof as described above or a complement thereof, in which the isolated nucleic acid is capable of specifically encoding the polypeptide as described above. As mentioned above, the polypeptide binds with high affinity to HLA-A0201 and thus can be presented by HLA-A0201-expressing presenting cells to CTL cells or TIL cells for activation of specific T cell immunity. Therefore, the polypeptide expressed by the isolated nucleic acid proposed in an embodiment of the present disclosure under a suitable condition can be used to prevent or treat a tumor, especially the polypeptide-expressing tumor from the HLA-A0201 positive subject, the safety and effectiveness of the treatment or prevention are improved.

Noted, it should be understood by skilled in the art that the nucleic acid mentioned in the description and claims of the present disclosure in fact refers to either or both chains of complementary double-strands of the polypeptide. For convenience, only one chain is disclosed in most cases in the description and claims of the present disclosure; however it means that another chain complemented is also disclosed. Besides, the nucleic acid in the present disclosure can be both in a DNA form and in a RNA form, and the disclosure to either form means both forms are disclosed.

Accordingly, in another aspect of the present disclosure, provided in embodiments is a nucleic acid construct. According to an embodiment of the present disclosure, the nucleic acid construct includes an encoding sequence, in which the encoding sequence is the nucleic acid as described above, and optionally a control sequence operably connected to the encoding sequence, in which the control sequence is one or more control sequences capable of directing the expression of the polypeptide in a host cell. According to an embodiment of the present disclosure, the control sequence includes but is not limited to U6 promoter, H1 promoter, CMV promoter, EF-1 promoter, LTR promoter or RSV promoter. Therefore, after transfected or infected a suitable condition with the nucleic acid construct proposed in an embodiment of the present disclosure which is connected with a vector under, the suitable host cell can efficiently express the polypeptide as described above, thus being capable of specifically preventing or treating a tumor in an effective way, particularly the polypeptide-expressing tumor from the HLA-A0201 positive subject.

Accordingly, in another aspect of the present disclosure, provided in embodiments is an expression vector. According to an embodiment of the present disclosure, the expression vector includes the nucleic acid construct as described above, including but is not limited to a retrovirus vector, a lentiviral vector and/or an adenovirus-associated virus vector. Therefore, after transfected or infected with the expression vector proposed in embodiments of the present disclosure under a suitable condition, the host cell can efficiently express the polypeptide as described above, thus being capable of specifically preventing or treating a tumor in an effective way, particularly the polypeptide-expressing tumor from the HLA-A0201 positive subject.

Accordingly, in another aspect of the present disclosure, provided in embodiments is a host cell. According to an embodiment of the present disclosure, the host cell carries the nucleic acid construct or the expression vector as described above, optionally obtained by transfecting or transforming the nucleic acid construct or the expression vector, in which the transfection or transformation can be conducted by means of electrotransformation, viral transfection or competent cell transformation, depending on the properties of the host cell and of the nucleic acid construct or the expression vector, as long as the polypeptide as described above can be efficiently expressed in the host cell without affecting the good status of the host cell. According to an embodiment of the present disclosure, the host cell can efficiently express the polypeptide as described above under a suitable condition, thus being capable of specifically preventing or treating a tumor in an effective way, particularly the polypeptide-expressing tumor from the HLA-A0201 positive subject.

It should be noted, the term "suitable condition" described in the description of the present disclosure refer to the condition which is suitable for the expression of the polypeptide described in the present disclosure. It would be easily understood by skilled in the art that the condition suitable for expressing the polypeptide includes but is not limited to suitable method of transformation or transfection, suitable conditions for transformation or transfection, good status of host cell, appropriate density of the host cell, suitable environment and appropriate period for cell culture. The term "suitable condition" is not particularly limited, and the condition for expressing the polypeptide can be optimized by skilled in the art according to the particular environment of the laboratory.

In still another aspect of the present disclosure, provided in embodiments is a pharmaceutical composition. According to an embodiment of the present disclosure, the pharmaceutical composition includes the polypeptide as described above, and a pharmaceutically acceptable adjuvant. It is discovered by the present inventors through a lot of experiments that the pharmaceutical composition including the polypeptide as described above and the pharmaceutically acceptable adjuvant can significantly stimulate the proliferation and secretion of CTL cells or TIL cells, remarkably killing the tumor cell which expresses the polypeptide as an antigen, thus exhibiting an efficacy of significantly preventing or treating a tumor, particularly the tumor specifically overexpressing the polypeptide as an antigen.

In still another aspect of the present disclosure, provided in embodiments is an antigen-presenting cell. According to an embodiment of the present disclosure, the antigen-presenting cell can present the polypeptide as described above. According to an embodiment of the present disclosure, the antigen-presenting cell presenting the polypeptide can effectively induce an immune response by the tumor-specific polypeptide as described above (as an antigen) in a subject, thus activating the function of specific CTL killing. The antigen-presenting cell proposed in an embodiment of the present disclosure has a remarkable efficacy of treating the polypeptide-expressing tumor from the HLA-A0201 positive subject with significant therapeutic efficacy and high safety.

According to a particular embodiment of the present disclosure, the antigen-presenting cell is obtained by at least one of the following steps: contacting a cell capable of presenting an antigen with the polypeptide, and introducing the nucleic acid, the nucleic acid construct or the expression vector as described above into a cell capable of presenting an antigen. It is discovered by the present inventors through experiments that the antigen-presenting cell can efficiently present the polypeptide by one or more means as described above, so that the polypeptide can be exposed on the surface of the antigen-presenting cell, thus being capable of efficiently inducing an immune response by the tumor-specific polypeptide as described above (as an antigen) in a subject, thereby further activating the function of specific CTL killing.

According to a particular embodiment of the present disclosure, the antigen-presenting cell is a dendritic cell which is characterized by high antigen endocytic and processing activity for presenting an antigen on the surface of cell. The dendritic cell is selected by the present inventors as an antigen-presenting cell, which allows initiation, regulation and maintenance of a stronger immune response against the polypeptide in the body.

In still another aspect of the present disclosure, provided in embodiments is an immune effector cell. According to an embodiment of the present disclosure, the immune effector cell can recognize the polypeptide or the antigen-presenting cell presenting the polypeptide as described above on its surface. According to an embodiment of the present disclosure, the immune effector cell is obtained by contacting the antigen-presenting cell as described above with a cell with immunogenicity. It is found by the present inventors that by such a contact, the antigen-presenting cell presenting the polypeptide is capable of activating a non-activated cell with immunogenicity, thus generating a great amount of immune effector cells which specifically kills target cells expressing the polypeptide as an antigen. According to another particular embodiment of the present disclosure, the cell with immunogenicity is T lymphocyte, such as $CD8^+$ T cell which can be activated to a greater extend by the antigen-presenting cell, with the activated $CD8^+$ T cell having a stronger activity in specifically killing the target cells expressing the polypeptide as an antigen.

In still another aspect of the present disclosure, provided in embodiments is a vaccine. According to an embodiment of the present disclosure, the vaccine includes the nucleic acid, the nucleic acid construct, the expression vector, the host cell, the antigen-presenting cell, or the immune effector cell as described above. As mentioned above, after transfected or infected under a suitable condition with the nucleic acid, the nucleic acid construct or the expression vector proposed in embodiments of the present disclosure, the host cell can express the polypeptide as described above, thus the nucleic acid, the nucleic acid construct, and the expression vector in embodiments of the present disclosure each can be used for preventing or treating the polypeptide-expressing tumor; further the antigen-presenting cell proposed in embodiments of the present disclosure has a significant efficacy in treating the polypeptide-expressing tumor from the HLA-A0201 positive subject; and furthermore the immune effector cell proposed in embodiments of the present disclosure has a significant efficacy in specifically killing a target cell expressing the polypeptide as an antigen. Thus, the vaccine proposed in embodiments of the present disclosure which includes the nucleic acid, the nucleic acid construct, the expression vector, the host cell, the antigen-presenting cell or the immune effector cell as described above, has a significant efficacy of preventing or treating the polypeptide-expressing tumor from the HLA-A0201 positive subject with higher safety and lower side effect.

In still another aspect of the present disclosure, provided in embodiments is an antibody. According to an embodiment of the present disclosure, the antibody specifically recognizes the polypeptide as described above. The antibody proposed in an embodiment of the present disclosure can specifically bind to said polypeptide, thereby being capable of specifically identifying a tumor cell which specifically overexpresses the polypeptide, thus the antibody proposed in the embodiment of the present disclosure plays a huge role in tumor diagnosis, treatment or prevention. Further, according to an embodiment of the present disclosure, the antibody can be obtained by collecting serum of an animal immunized with the polypeptide as described above, and isolating the antibody of interest from the serum. With the method for preparing an antibody according to an embodiment of the present disclosure, the antibody specifically recognizing the polypeptide can be obtained effectively in a convenient and rapid way, which can be used for diagnosis, treatment or prevention of tumor effectively.

In summary, the polypeptide proposed in embodiments of the present disclosure has many advantages, for example, the polypeptide has higher specificity against tumor due to exclusive presence in a tumor and absence in a tumor-tissue sample of a subject, resulting in the higher specificity of the immune response accordingly, with improved safety and lower side effect (i.e. rarely causing a severe adverse response) compared with other polypeptide vaccines against tumor; further it is easily to be artificially synthesized due to its simple structure, thus can be prepared as a vaccine or pharmaceutical composition against tumor. The mutant polypeptide depicted in GLKDLLNPI (SEQ ID NO: 1) or each of its variants can be used as a target or a vaccine for biologically treating the polypeptide-expressing tumor from the HLA-A0201 positive subject, thus inducing an immune response in the body. A composition of the polypeptide and an adjuvant, an antigen-presenting cell loaded with the polypeptide as a vaccine, or a polypeptide-specific DC-CTL or DC-CIK vaccine can be used to specifically kill tumor cells, for preventing or treating a cancer expressing the polypeptide, including but not limited to lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, brain tumor and the like.

Therapeutic Method

Further, provided in embodiments is a therapeutic method. According to embodiments of the present disclosure, the therapeutic method includes administering to a subject a therapeutically effective amount of the polypeptide, the nucleic acid, the nucleic acid construct, the expression vector, the host cell, the pharmaceutical composition, the antigen-presenting cell, the immune effector cell, the vaccine or the antibody as described above. As mentioned above, the therapeutic method proposed in an embodiment of the present disclosure including administering a therapeutically effective amount of any of the polypeptide, the nucleic acid, the nucleic acid construct, the expression vector, the host cell, the pharmaceutical composition, the antigen-presenting cell, the immune effector cell, the vaccine and the antibody as described above is capable of effectively treating or preventing the polypeptide-expressing tumor from the HLA-A0201 positive subject.

The terms "administer", "administering", "administered", "administration" and the like as used herein refer to introducing a predetermined amount of a substance into a subject in any suitable manner. The polypeptide, nucleic acid, nucleic acid construct, expression vector, host cell, pharmaceutical composition, antigen-presenting cell, immune effector cell, vaccine or antibody in embodiments of the present disclosure can be administered by any common route provided that they can reach the expected focus. Various routes of administration are contemplated, including but not limited to peritoneal, venous, muscular, subcutaneous, cortical, oral, topical, nasal, pulmonary and rectal. Further, the composition for oral administration should be coated or formulated to prevent its active component from degrading in the stomach. For example, the composition of the present disclosure can be administered in an injectable preparation. Furthermore, the pharmaceutical composition of the present disclosure can be administered by using specific devices that deliver its active component to target cells.

The frequency and dose of administration of the polypeptide, nucleic acid, nucleic acid construct, expression vector, host cell, pharmaceutical composition, antigen-presenting cell, vaccine or antibody in embodiments of the present disclosure can be determined depending on the type of disease to be treated, the route of administration, the age, sex, body weight of a subject, the severity of disease, and dosage form of medicament containing an active component. According to some embodiments of the present disclosure, the daily dose may be divided into 1 dose, 2 doses or multiple doses in a suitable form, for administration once, twice or multiple times throughout the time period, provided a therapeutically effective amount is achieved.

The term "therapeutically effective amount" as used herein refers to an amount sufficient to significantly ameliorate certain symptoms associated with a disease or condition, that is, an amount that provides a therapeutic effect for a given condition or dosage regimen. The terms "therapy", "therapeutic", "treatment", "treat" and the like as used herein refer to achieving a desired pharmacological and/or physiological effect. As used herein, the "treatment" encompasses the administration of the polypeptide, nucleic acid, nucleic acid construct, expression vector, host cell, pharmaceutical composition, antigen-presenting cell, immune effector cell, vaccine or antibody in embodiments of the present disclosure to a subject for treatment, including but not limited to administer the polypeptide, the nucleic acid, the nucleic acid construct, the expression vector, the host cell, the pharmaceutical composition, the antigen-presenting cell, the immune effector cell, the vaccine or the antibody described in the present disclosure to an individual in need thereof.

Diagnostic Method

Further, provided in embodiments is a diagnostic method. According to an embodiment of the present disclosure, the diagnostic method includes detecting whether a biological sample derived from a subject contains the polypeptide or the fragment thereof as described above, and determining whether the subject suffers from a tumor based on the presence or absence of the polypeptide in the biological sample. The polypeptide (as a tumor marker for cancer diagnosis due to its exclusive presence in a tumor) free in serum can be detected by the mass spectrometry, so as to determine whether a subject suffers from a cancer or not. It is found by the present inventors that the polypeptide is specifically overexpressed in a tumor, thus the diagnostic method proposed in the embodiment of the present disclosure can be used to effectively diagnose whether a subject suffers from a tumor where the polypeptide is specifically overexpressed.

Furthermore, the present inventors still found that the polypeptide is specifically overexpressed in a tumor selected from one or more of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia and brain tumor, especially breast cancer, thus the accuracy of diagnosing the tumor as described above (especially breast cancer) can be further improved by using the diagnostic method proposed in the embodiment of the present disclosure.

Meanwhile, the present inventors yet still found that HLA-A0201 is present in Chinese populations in a high proportion, thus the accuracy of diagnosis of the polypeptide-expressing tumor from the HLA-A0201 positive subject can be improved by using the diagnostic method proposed in the embodiment of the present disclosure.

Diagnostic System

Furthermore, provided in embodiments is a diagnostic system. According to an embodiment of the present disclosure, referring to FIG. 1, the diagnostic system includes a polypeptide detecting device 100, configured to detect whether a biological sample derived from a subject contains the polypeptide as described above; and a diagnosis determining device 200, connected to the polypeptide determining device 100 and configured to determine whether the subject suffers from a tumor based on the presence or absence of the polypeptide in the biological sample. According to a particular embodiment of the present disclosure, whether the free polypeptide is present in serum of the subject can be detected by a mass spectrometer, for determination of presence or absence of the free polypeptide by an analysis device for mass spectrometry data, thus determining whether a subject suffers from a tumor. It is found by the present inventors that the polypeptide is specifically overexpressed in a tumor, thus the diagnostic system proposed in the embodiment of the present disclosure can be used to effectively diagnose whether a subject suffers from a tumor where the polypeptide is specifically overexpressed.

Furthermore, the present inventors still found that the polypeptide is specifically overexpressed in a tumor selected from one or more of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia and brain tumor, especially breast cancer, thus the accuracy of diagnosing the tumor as described above (especially breast cancer) can be further improved by using the diagnostic system proposed in the embodiment of the present disclosure.

Meanwhile, the present inventors yet still found that HLA-A0201 is present in Chinese populations in a high proportion, which binds with strong affinity to the polypeptide for activation of a serious of immune responses, thus the accuracy of diagnosis of the polypeptide-expressing tumor from the HLA-A0201 positive subject is improved by using the diagnostic system proposed in the embodiment of the present disclosure.

It should be noted that the polypeptide according to embodiments of the present disclosure and the use thereof, the nucleic acid encoding the polypeptide, nucleic acid construct, expression vector, host cell, pharmaceutical composition, antigen-presenting cell, immune effector cell, vaccine and antibody, and the therapeutic method, diagnostic method and diagnostic system are discovered and achieved by the present inventors through lots of creative labor and optimization.

The technical solutions of the present disclosure will be explained below in combination with the embodiments. It will be appreciated by skilled in the art that the following examples are explanatory, and cannot be construed to limit the scope of the present disclosure. The particular techniques or conditions not specified in the examples can be performed according to the techniques or conditions described in literatures in the art or according to the product instructions. In addition, the reagents or instruments not indicated the manufacturer may be commercially available, for example, obtained from Illumina.

Example 1 Prediction of Polypeptide Affinity

With a lot of screening experiments, it is found by the present inventors that the mutation occurring in the wild-type PIK3CA gene (where the encoded protein plays a role of phosphotransferase in serine/threonine kinase), causes the amino acid encoded at position 453 to be mutated into Lysine (i.e. Lys or K) from Glutamic acid (i.e. Glu or E). The mutated PIK3CA gene is specifically expressed at a high level in tumor, and the mutant polypeptide encoded is specific to tumor and is capable of binding with high affinity to HLA-A0201. Such the binding activity has been verified by the present inventors through experiments (shown as below).

In order to develop more valuable biologic drugs for clinic use, particular in cancer therapy, the present inventors selected a portion amino acid sequences of protein encoded by PIK3CA gene including the amino acid Glutamic acid (i.e. Glu or E) at position 453 as the wild-type polypeptide (SEQ ID NO: 5); selected a mutant polypeptide (SEQ ID NO: 1) where the amino acid Glutamic acid (i.e. Glu or E) at position 453 is mutated into Lysine (i.e. Lys or K); and designed several variants based on the mutant polypeptide (SEQ ID NO: 1) with expectation of maintaining the high affinity to HLA-A0201 without sacrificing immunogenicity. Here only shows results of the wild-type polypeptides (SEQ ID NO: 5), the mutant polypeptide (SEQ ID NO: 1) and some mutant polypeptide' variants (SEQ ID NOs: 2-4) which were determined to be useful.

The affinity of the wild-type polypeptides (SEQ ID NO: 5), the mutant polypeptide (SEQ ID NO: 1) or the mutant polypeptide' variants (SEQ ID NOs:2-4) to a selected HLA allele (i.e., the subtype HLA-A0201) was respectively predicted by using independently developed software (prediction software of mutant polypeptide's affinity based on the tumor DNA and RNA sequencing, software copyright No: 2016SR002835), with prediction results represented in $IC_{50}$ scores, where $IC_{50}$ score below 500 nM indicating presence of affinity, and $IC_{50}$ score below 50 nM indicating high affinity. The present inventors have predicted the affinity of the wild-type polypeptide (depicted in GLEDLLNPI, SEQ ID NO: 5), the mutant polypeptide (depicted in GLKDLLNPI, SEQ ID NO:1), the mutant polypeptide's variant (depicted in GLKDLLNPL, SEQ ID NO:2), the mutant polypeptide's variant (depicted in GMKDLLNPL, SEQ ID NO: 3) and the mutant polypeptide's variant (depicted in GMKDLLNPI, SEQ ID NO: 4) respectively, thus screening out those polypeptides whose $IC_{50}$ scores are not only below 500 nM, but also lower than that of the wild-type polypeptide. Table 1 shows the prediction results of affinity of polypeptides. Further, the affinity between the polypeptides screened and T2 cells was verified in next steps.

TABLE 1

Prediction results of affinity between polypeptides and HLA-A0201

| Sequences of mutant polypeptide and its variants | IC$_{50}$ (nM) | Sequence of wild-type polypeptide | IC$_{50}$ (nM) |
|---|---|---|---|
| GLKDLLNPI (SEQ ID NO: 1) | 2.57 | GLEDLLNPI (SEQ ID NO: 5) | 6.68 |
| GLKDLLNPL (SEQ ID NO: 2) | 2.24 | GLEDLLNPI (SEQ ID NO: 5) | 6.68 |
| GMKDLLNPL (SEQ ID NO: 3) | 3.01 | GLEDLLNPI (SEQ ID NO: 5) | 6.68 |
| GMKDLLNPI (SEQ ID NO: 4) | 2.89 | GLEDLLNPI (SEQ ID NO: 5) | 6.68 |

With prediction by the software, the mutant polypeptide and its variants all have an IC$_{50}$ score below 50 nM with high affinity; further all the IC$_{50}$ scores are lower than that of the wild-type polypeptide (depicted in GLEDLLNPI, SEQ ID NO: 5), thus indicating that the affinity of those polypeptides is higher than that of the wild-type polypeptide.

Example 2 Validation of Affinity Between Polypeptide and T2 Cells 2.1 Synthesis and Purification of Polypeptides The various types of polypeptides involved in the example of the present disclosure were synthesized by the standard solid phase peptide synthesis, followed by purification with the reverse phase HPLC, where its purity (>90%) is identified by the HPLC method and its identity is determined by the mass spectrometry.

2.2 Affinity Verification

T2 cells, as a hybridoma cell of HLA-A2 positive-T lymphocyte and B lymphocyte, can express HLA-A0201 on its surface, but could not transfer endogenous antigens due to the deficiency of the essential transporter associated with antigen processing (TAP) protein complex in the endogenous antigen presentation pathway. The T2 cells were purchased from ATCC (Cat. No.: CRL-1992).

To a 24-well plate containing T2 cells (in 2×10$^5$ cells/well) resuspended with 500 µL serum-free Iscove's Modified Dulbecco's Medium (IMDM) which contains human β2 microglobulin in a final concentration of 3 µg/ml, added with the synthetic wild-type polypeptide (depicted in GLEDLLNPI, SEQ ID NO: 5), the mutant polypeptide (depicted in GLKDLLNPI, SEQ ID NO: 1), the mutant polypeptide's variant (depicted in GLKDLLNPL, SEQ ID NO:2), the mutant polypeptide's variant (depicted in GMKDLLNPL, SEQ ID NO: 3) and the mutant polypeptide's variant (depicted in GMKDLLNPI, SEQ ID NO: 4) (each in a final concentration of 100 µM) respectively, followed by incubation in an incubator under 37° C. and 5% CO$_2$ overnight, in duplicate for each group, where the well containing T2 cells alone is used as a background control, and the well containing T2 cells and CMV polypeptide (depicted in NLVPMVATV, SEQ ID NO: 6) is used as a positive control. After centrifugation at 200 g for 5 minutes for cell collection, the collected cells were washed with phosphate buffer saline (PBS) buffer twice, before incubated with anti-HLA-A*02:01 FITC monoclonal antibody at 4° C. for 30 minutes. The mean fluorescence intensity of cells was then detected and analyzed by the flow cytometry (BD FACSJazz™)) and its software.

The fluorescence index (FI) was calculated using the following formula:

FI=[mean fluorescence intensity (MFI) of sample−MFI of background]/MFI of background, where MFI of background represents the value in the absence of polypeptide, with FI>1.5 indicating high affinity between the polypeptide and HLA-A*0201 molecule, 1.0<FI<1.5 indicating moderate affinity between the polypeptide and HLA-A*0201 molecule, and 0.5<FI<1.0 indicating low affinity between the polypeptide and HLA-A*0201 molecule.

Figure 2:
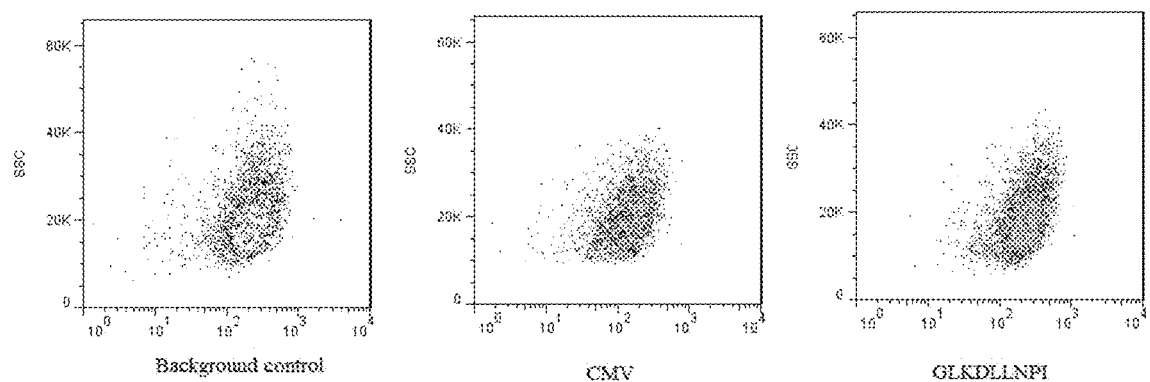
FIG. 2 is a graph showing affinity results of T2 cells loaded with the polypeptide to HLA-A0201 detected by flow cytometry according to an embodiment of the present disclosure.

The detection results of affinity of the polypeptides are shown in Table 2 and FIG. 2.

TABLE 2

Detection results of affinity between polypeptides and HLA-A0201

| Samples | Concentration of polypeptide | Mean fluorescence intensity | FI | Conclusion |
|---|---|---|---|---|
| GLEDLLNPI (SEQ ID NO: 5) | 100 µM | 780 | 2.24 | high affinity |
| GLKDLLNPI (SEQ ID NO: 1) | 100 µM | 752 | 2.12 | high affinity |
| GLKDLLNPL (SEQ ID NO: 2) | 100 µM | 712 | 1.95 | high affinity |
| GMKDLLNPL (SEQ ID NO: 3) | 100 µM | 761 | 2.16 | high affinity |
| GMKDLLNPI (SEQ ID NO: 4) | 100 µM | 730 | 2.03 | high affinity |
| Background control | 0 µM | 241 | 0.00 | no affinity |
| CMV positive control | 100 µM | 658 | 1.73 | high affinity |

It was verified by experiments that the FI of the background control and the CMV positive control are respectively 0 and 1.73, both in a normal range, while the FIs of the wild-type polypeptide (depicted in GLEDLLNPI, SEQ ID NO: 5), the mutant polypeptide (depicted in GLKDLLNPI, SEQ ID NO:1), the mutant polypeptide's variant (depicted in GLKDLLNPL, SEQ ID NO:2), the mutant polypeptide's variant (depicted in GMKDLLNPL, SEQ ID NO: 3) and the mutant polypeptide's variant (depicted in GMKDLLNPI, SEQ ID NO: 4) are each above 1.5, further demonstrating high affinity of the wild-type polypeptide, as well as the mutant polypeptide and its five variants to HLA-A0201 molecule.

Example 3 In Vitro Stimulation of CD8+ T Cells by Polypeptide

Peripheral blood mononuclear cells (PBMCs) in 100 mL peripheral blood obtained from a HLA-A0201-positive healthy volunteer were isolated using the Ficoll solution, where CD8+ T cells among the PBMCs were isolated with CD8 magnetic beads, and monocytes among the PBMCs were incubated by an adherence method. Such the monocytes were induced into immature dendritic cells (DCs) in the presence of GM-CSF (1000 U/ml) and IL-4 (1000 U/ml), followed by inducing to polypeptide-specific mature DCs in the presence of IFN-γ (100 U/ml) and LPS (10 ng/ml) as well as the subsequently added with the mutant polypeptide (depicted in GLKDLLNPI, SEQ ID NO: 1), the mutant polypeptide's variant (depicted in GLKDLLNPL, SEQ ID NO:2), the mutant polypeptide's variant (depicted in GMKDLLNPL, SEQ ID NO: 3) and the mutant polypeptide's variant (depicted in GMKDLLNPI, SEQ ID NO: 4), respectively.

The CD8+ T cells from the volunteer in a well were incubated with the mature DCs obtained, along with IL-21, with addition of IL-2 and IL-7 after 3 days' culture and addition IL-2 and IL-7 again at day 5 and day 7 respectively, after which the collected mixture of cells were counted on day 10, for use in the next enzyme-linked immune-spot assay (ELISPOT) and lactate dehydrogenase (LDH) assay. The counting results are shown in Table 3.

TABLE 3

Results of cell counting after incubation

| | Total number of cells before incubation | Total number of cells after incubation |
|---|---|---|
| GLEDLLNPI (SEQ ID NO: 5) | $2.0 \times 10^6$ | $8.6 \times 10^6$ |
| GLKDLLNPI (SEQ ID NO: 1) | $2.0 \times 10^6$ | $9.6 \times 10^6$ |
| GLKDLLNPL (SEQ ID NO: 2) | $2.0 \times 10^6$ | $7.6 \times 10^6$ |
| GMKDLLNPL (SEQ ID NO: 3) | $2.0 \times 10^6$ | $8.9 \times 10^6$ |
| GMKDLLNPI (SEQ ID NO: 4) | $2.0 \times 10^6$ | $8.1 \times 10^6$ |

With 10 days of incubation, the cells have proliferated significantly, about 3-5 times more than that before incubation.

Example 4 ELISPOT Validation of CD8+ T Cell Immune Response Activated by Polypeptide The mixture of cells collected in the example 3 were incubated with T2 cells loaded with the mutant polypeptide (depicted in GLKDLLNPI, SEQ ID NO: 1) or the wild-type polypeptide (depicted in GLEDLLNPI, SEQ ID NO: 5) respectively in an plate containing human Interferon-γ (IFN-γ) for the ELISPOT assay, by which the spots produced were counted. The well containing T2 cells loaded with the mutant polypeptide is an experimental well, and the well containing T2 cells loaded with the wild-type polypeptide is a control well. The mutant polypeptide with immunogenicity should meet the following requirement:

Spots number of mutant polypeptide/spots number of wild-type polypeptide >2, where the number of spots produced by the mutant polypeptide more than two times of the number of spots produced by the wild-type polypeptide indicates the mutant polypeptide has immunogenicity.

Figure 3:
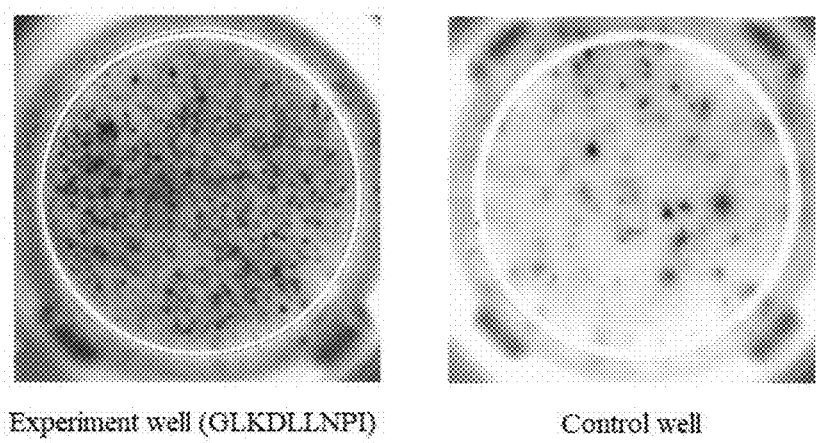
FIG. 3 is a graph showing activation of an immune response of $CD8^+$ T cell by the polypeptide verified by ELISPOTs method according to an embodiment of the present disclosure; the sequence GLKDLLNPI is SEQ ID NO: 1.

The detection results are shown in Table 4 and FIG. 3.

The reaction principle of ELISPOT assay is as follows: CD8$^+$ T cells can specifically recognize the complex of HLA-A0201 and the polypeptide, with different T cell populations recognizing different complexes of HLA-A0201 and the polypeptides with different sequences, thus the CD8$^+$ T cell is capable of specifically recognizing the T2 cells loaded with the mutant polypeptide (depicted in GLKDLLNPI, SEQ ID NO: 1), but could not recognize the T2 cells loaded with the wild-type polypeptide (depicted in GLEDLLNPI, SEQ ID NO: 5). After specifically recognizing the complex of HLA-A0201 and the mutant polypeptide, the polypeptide specific-CD8$^+$ T cell is activated and secretes IFN-γ, which will be captured by the firstly antibody coated on the ELISPOT plate and further be bound by an enzyme-coupled secondly antibody, and finally developed by addition of a substrate which can be catalyzed by the enzyme, thus forming colored spots. The number of spots produced represents the number of the IFN-γ secreted by the activated CD8$^+$ T cell.

TABLE 4

Results of IFN-γ secreted by polypeptide-specific CD8 of polypeptide

| Sequences of mutant polypeptide or its variants activating T cells | Number of spots produced by mutant polypeptide or each of its variants | Number of spots produced by wild-type polypeptide | Ratio of mutant polypeptide to wild-type polypeptide | Conclusion |
|---|---|---|---|---|
| GLKDLLNPI (SEQ ID NO: 1) | 361 | 81 | 4.4 | immunogenic |
| GLKDLLNPL (SEQ ID NO: 2) | 327 | 60 | 5.5 | immunogenic |
| GMKDLLNPL (SEQ ID NO: 3) | 389 | 79 | 4.9 | immunogenic |
| GMKDLLNPI (SEQ ID NO: 4) | 359 | 77 | 4.7 | immunogenic |

Example 5 Demonstration of CD8$^+$ T Cell Killing Activity by LDH Release Assay

The mixture of cells collected in the example 3 were incubated with the T2 cells loaded with the mutant polypeptide (depicted in GLKDLLNPI, SEQ ID NO: 1), the T2 cells loaded with the mutant polypeptide's variant (depicted in GLKDLLNPL, SEQ ID NO:2), the T2 cells loaded with the mutant polypeptide's variant (depicted in GMKDLLNPL, SEQ ID NO: 3), the T2 cells loaded with the mutant polypeptide's variant (depicted in GMKDLLNPI, SEQ ID NO: 4), the T2 cells loaded with the wild-type polypeptide (depicted in GLEDLLNPI, SEQ ID NO: 5), and the T2 cells without polypeptide respectively for 4 hours; after which 50 μL cell supernatant collected from each well was individually added into 50 μL substrate mixture of LDH for catalyzation of the LDH substrate, and the absorbance at wavelengths of 490 nm and 680 nm (as a reference) is measured, where a maximum release well, a volume correction well, a medium alone well, a spontaneous release well of effector cell and a spontaneous release well of target well as different control wells, as well effector cells (T cells) and target cells (T2 cell) in different ratios as experiment wells are set in triplicate.

The killing efficiency of CD8$^+$ T cells to T2 cells is calculated by the following formula:

Killing efficiency (%)=(experiment well−spontaneous release well of effector cell−spontaneous release well of target well+medium alone well)/(maximum release well of target well−volume correction well−spontaneous release well of target well+medium alone well)×100%.

The reaction principle of the LDH release assay is as follows: the lactate dehydrogenase (LDH) is one of the endoenzyme in cytoplasm of live cells, which could not penetrate the cell membrane under a normal condition, however when the target cells are attacked and damaged by the effector cells, resulting in the change of cell membrane permeability, the LDH can be released into the medium, thereby reducing the oxidized coenzyme I (NAD+) into NADH in the process of catalyzing lactic acid to pyruvate, with the latter NADH formed into a colored formazan compound (which exhibits a high absorption peak at a wavelength of 490 nm or 570 nm) in the presence of a hydrogen donor (phenazine dimethyl sulfate, PMS) and reduced Iodonitrotetrazolium chloride (INT) or Nitrotetrazolium Blue chloride (NBT), thus the viability of effector cells can be calculated according to the OD value. The results are shown in Table 5 and FIG. 4.

TABLE 5

Results of specific recognition and killing of target cells Loaded with polypeptide by T cells

| Groups | Ratio of effector cells to target cells (1:1) | Ratio of effector cells to target cells (10:1) |
|---|---|---|
| T cells (GLKDLLNPI, SEQ ID NO: 1) + T2 cells (GLKDLLNPI, SEQ ID NO: 1) | 3.93% | 40.60% |
| T cells (GLKDLLNPI, SEQ ID NO: 1) + T2 cells (GLEDLLNPI, SEQ ID NO: 5) | 2.73% | 4.83% |
| T cells (GLKDLLNPL, SEQ ID NO: 2) + T2 cells (GLKDLLNPL, SEQ ID NO: 2) | 3.85% | 32.13% |
| T cells (GLKDLLNPL, SEQ ID NO: 2) + T2 cells (GLEDLLNPI, SEQ ID NO: 5) | 3.43% | 3.56% |
| T cells (GMKDLLNPL, SEQ ID NO: 3) + T2 cells GMKDLLNPL, SEQ ID NO: 3) | 3.57% | 45.73% |
| T cells (GMKDLLNPL, SEQ ID NO: 3) + T2 cells (GLEDLLNPI, SEQ ID NO: 5) | 4.56% | 5.82% |
| T cells (GMKDLLNPI, SEQ ID NO: 4) + T2 cells (GMKDLLNPI, SEQ ID NO: 4) | 4.93% | 35.06% |
| T cells (GMKDLLNPI, SEQ ID NO: 4) + T2 cell (GLEDLLNPI, SEQ ID NO: 5) | 3.52% | 5.21% |

Figure 4:
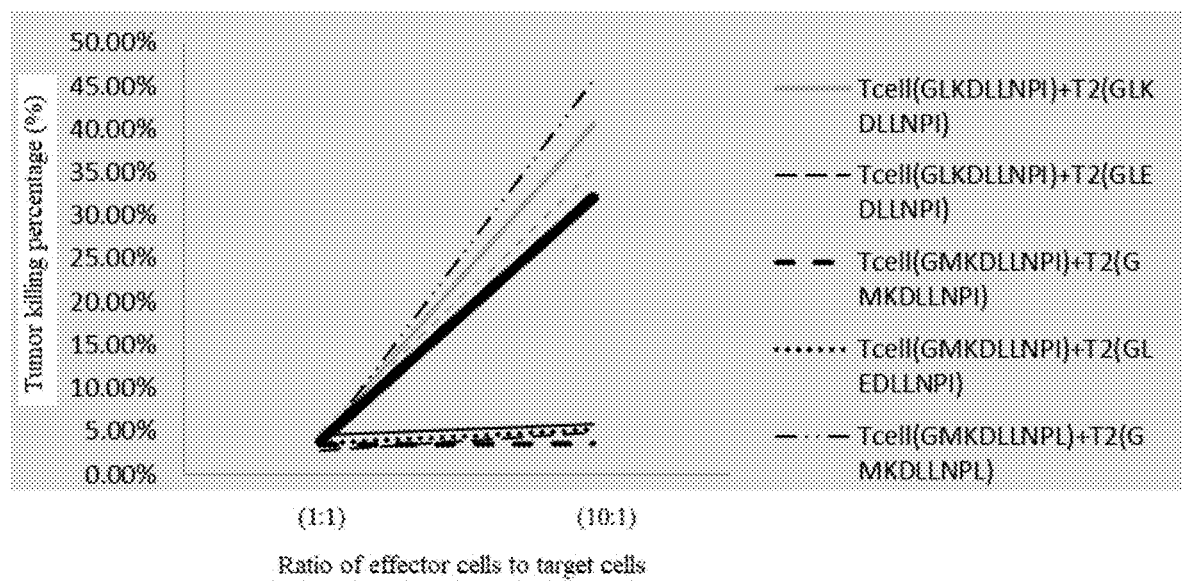
FIG. 4 is a graph showing specific killing of target cells loaded with the polypeptide by activated $CD8^+$ T cells according to an embodiment of the present disclosure; the sequences shown are (SEQ ID NO: 1) GLKDLLNPI (SEQ ID NO: 2) GLKDLLNPL (SEQ ID NO: 3) GMKDLLNPL (SEQ ID NO: 4), GMKDLLNPI and GLEDLLNPI (SEQ ID NO: 5)

As can be seen from Table 5 and FIG. 4, the T cells activated by the mutant polypeptide (depicted in GLKDLLNPI, SEQ ID NO:1), the mutant polypeptide's variant (depicted in GLKDLLNPL, SEQ ID NO:2), the mutant polypeptide's variant (depicted in GMKDLLNPL, SEQ ID NO: 3) or the mutant polypeptide's variant (depicted in GMKDLLNPI, SEQ ID NO: 4) at a ratio of effector cells to target cells of 1:1 or 10:1, is capable of killing the corresponding T2 cells loaded with the mutant polypeptide (depicted in GLKDLLNPI, SEQ ID NO: 1) or each of the three variants respectively, but could not kill the T2 cells loaded with the wild-type polypeptide (depicted in GLEDLLNPI, SEQ ID NO: 5), thus further demonstrating the T cells activated by the mutant polypeptide (depicted in GLKDLLNPI, SEQ ID NO:1), the mutant polypeptide's variant (depicted in GLKDLLNPL, SEQ ID NO:2), the mutant polypeptide's variant (depicted in GMKDLLNPL, SEQ ID NO: 3) or the mutant polypeptide's variant (depicted in GMKDLLNPI, SEQ ID NO: 4) are all capable of specifically killing the corresponding target cells loaded with the mutant polypeptide (depicted in GLKDLLNPI, SEQ ID NO:1) or each of the three variants (SEQ ID NOs:2-4) respectively.

Example 6 Establishment of Subcutaneously Implanted Tumor Model with MCF7 Cell Line Expressing Polypeptide GLKDLLNPI (SEQ ID NO: 1) or Each of its Variants 6.1 Construction of a Recombinant Lentiviral Vector Expressing Polypeptide GLKDLLNPI (SEQ ID NO: 1) or Each of its Variants and Packaging of Each Corresponding Lentivirus The DNA sequence encoding the mutant polypeptide (depicted in GLKDLLNPI, SEQ ID NO: 1) is shown as ATGGATTAGAAGATTTGCTGAACCCTA(SEQ ID NO:7);

the DNA sequence encoding a variant of the mutant polypeptide (depicted in GLKDLLNPL, SEQ ID NO:2) is shown as ATGGATTAGAAGATTTGCTGAACCTTA(SEQ ID NO:8);

the DNA sequence encoding another variant of the mutant polypeptide (depicted in GMKDLLNPL, SEQ ID NO: 3) is shown as ATGATGTAGAAGATTTGCTGAACCT(SEQ ID NO:9);

the DNA sequence encoding still another variant of the mutant polypeptide (depicted in GMKDLLNPI, SEQ ID NO: 4) is shown as ATGGATTAGAAGATTTGCT-GAACCGTA (SEQ ID NO:10); and the DNA sequence encoding the wild-type polypeptide (depicted in GLEDLLNPI, SEQ ID NO: 5) is shown as ATGGATGAAAAGATTTGCTGAACCCTA(SEQ ID NO:11).

A lentiviral vector pHBLV-Puro expressing the wild-type polypeptide (depicted in GLEDLLNPI, SEQ ID NO: 5) was constructed and named as pHBLV-Puro-GLEDLLNPI;

a lentiviral vector pHBLV-Puro expressing the mutant polypeptide (depicted in GLKDLLNPI, SEQ ID NO:1) was constructed and named as pHBLV-Puro-GLKDLLNPI;

a lentiviral vector pHBLV-Puro expressing a mutant polypeptide's variant (depicted in GLKDLLNPL, SEQ ID NO:2) was constructed and named as pHBLV-Puro-GLKDLLNPL;

a lentiviral vector pHBLV-Puro expressing a mutant polypeptide's variant (depicted in GMKDLLNPL, SEQ ID NO:3) was constructed and named as pHBLV-Puro-GMKDLLNPL; and a lentiviral vector pHBLV-Puro expressing a mutant polypeptide's variant (depicted in GMKDLLNPI, SEQ ID NO:4) was constructed and named as pHBLV-Puro-GMKDLLNPI.

In the presence of plasmids pSPAX2 and pMD2G, such five lentiviral vectors each were used to co-transfect 293T cells for packaging lentivirus, thus obtaining lentivirus expressing the wild-type polypeptide (depicted in GLEDLLNPI, SEQ ID NO: 5), lentivirus expressing the mutant polypeptide (depicted in GLKDLLNPI, SEQ ID NO:

1), lentivirus expressing the mutant polypeptide's variant (depicted in GLKDLLNPL, SEQ ID NO: 2), lentivirus expressing the mutant polypeptide's variant (depicted in GMKDLLNPL, SEQ ID NO: 3), and lentivirus expressing the mutant polypeptide's variant (depicted in GMKDLLNPI, SEQ ID NO: 4), respectively.

6.2 Establishment of Human Breast Cancer Cell Line Expressing Polypeptide GLKDLLNPI (SEQ ID NO: 1)

The human breast cancer cell line MCF7 which is HLA-A*0201 positive was purchased from ATCC (Cat. No.: HTB-22). The cell line MCF7 was incubated in the Dulbecco's Modified Eagle Medium (DMEM) containing 10% fetal calf serum, 100 U/mL penicillin and 100 U/mL streptomycin in an incubator under 37° C. and 5% $CO_2$, and subsequently infected with the lentivirus expressing the mutant polypeptide (depicted in GLKDLLNPI, SEQ ID NO: 1) as prepared in 6.1. Afterwards, the infected cells were incubated with the Puromycin antibiotic for a certain duration to screen out those viable infected cells, i.e., obtaining the human breast cancer cell line MCF7 which expresses the mutant polypeptide (depicted in GLKDLLNPI, SEQ ID NO: 1) and named as the human breast cancer cell line MCF7-polypeptide GLKDLLNPI (SEQ ID NO: 1).

6.3 Human Immune Reconstruction to NOD SCID Mice

After isolated with Ficoll solution from 600 to 900 ml anticoagulant peripheral blood from a healthy volunteer, the collected PBMCs in a concentration of $2 \times 10^7$ cells/0.5 ml were intraperitoneally injected into each of 300 NOD SCID mice without immune leakage, so as to reconstruct a human immune system in the NOD SCID mice, with the mice after 4 weeks selected for subsequent inoculation of the human breast cancer cell line MCF7-polypeptide GLKDLLNPI obtained in 6.2.

6.4 Construction of Subcutaneous Human Breast Cancer-Modeled Mice

The human breast cancer cell line MCF7-polypeptide GLKDLLNPI (SEQ ID NO: 1) obtained in 6.2 was incubated in DMEM medium containing 10% fetal calf serum, 100 U/mL penicillin and 100 U/mL streptomycin in an incubator under 37° C. and 5% $CO_2$, and then the cells were centrifuged at 3000 rpm for collection. The collected cells were washed with sterile physiological saline three times, and then diluted appropriately. To 40 μl tumor cell suspension, 10 μl 0.4% phenol blue was added for staining, subsequently the tumor cell suspension in a concentration of $1 \times 10^8$ cells/ml was prepared after counting under microscope. 100 μl of the tumor cell suspension was inoculated into each of the NOD/SCID mice by subcutaneous injection at 4 weeks post immune reconstruction in 6.3, with daily observation of the presence/absence of infection at inoculation sites, the increase/decrease of tumor size (in the case of presence of a tumor), and measurement of the major axis (a) and the minor axis (b) of a tumor by a vernier caliper every 2 or 3 days (where the tumor size=a×b×b/2). After 7 days from inoculation, a tumor in a size of rice grain was touchable at the inoculation site. After that, the subcutaneous tumor-modeled NOD/SCID mice (modeled with MCF7-polypeptide GLKDLLNPI (SEQ ID NO:1)) were treated with a polypeptide+complete Freund's adjuvant vaccine, a polypeptide+DCs vaccine, a lentivirus-infected DCs vaccine and a DC-CTL vaccine respectively, with the tumor size and mouse survival rate observed and recorded every 2 days.

Example 7 Preparation of Polypeptide Vaccine and Therapeutic Regimen

The subcutaneous tumor-modeled NOD/SCID mice obtained in 6.4 of the example 6 were divided into 6 groups randomly as below, with 6 mice per group:

an adjuvant+wild-type polypeptide (depicted in GLEDLLNPI, SEQ ID NO: 5) group,
an adjuvant alone group,
an adjuvant+mutant polypeptide (depicted in GLKDLLNPI, SEQ ID NO: 1) group,
an adjuvant+mutant polypeptide's variant (depicted in GLKDLLNPL, SEQ ID NO:2) group,
an adjuvant+mutant polypeptide's variant (depicted in GMKDLLNPL, SEQ ID NO:3) group, and
an adjuvant+mutant polypeptide's variant (depicted in GMKDLLNPI, SEQ ID NO:4) group.

Except for the adjuvant alone group, mice in other 5 groups received first immunization, by subcutaneous injection at two sites of the mouse back with 100 μg wild-type polypeptide (depicted in GLEDLLNPI, SEQ ID NO: 5), 100 μg mutant polypeptide (depicted in GLKDLLNPI, SEQ ID NO: 1), 100 μg mutant polypeptide's variant (depicted in GLKDLLNPL, SEQ ID NO:2), 100 μg mutant polypeptide's variant (depicted in GMKDLLNPL, SEQ ID NO:3) and 100 μg mutant polypeptide's variant (depicted in GMKDLLNPI, SEQ ID NO:4) respectively, each of which was mixed with 150 μl Freund's complete adjuvant in PBS to a final volume of 300 μl. After 2 weeks, differently-immunized mice in 5 groups received respective same-dosage booster immunizations at two week interval for 4 times in total, with incomplete Freund's adjuvant for the latter three immunizations.

The general characteristics (including mental state, activity, response, diet, body weight and tumor growth) of the mice were observed daily, where the major axis (a) and the minor axis (b) of a tumor were measured by a vernier caliper every 2 days for calculation of tumor size according to a formula of a×b×b/2, where the mouse survival rate in a time period is calculated by the following formula:

Survival rate=the number of survival mice/(the number of survival mice+the number of dead mice)×100%.

Figure 5:
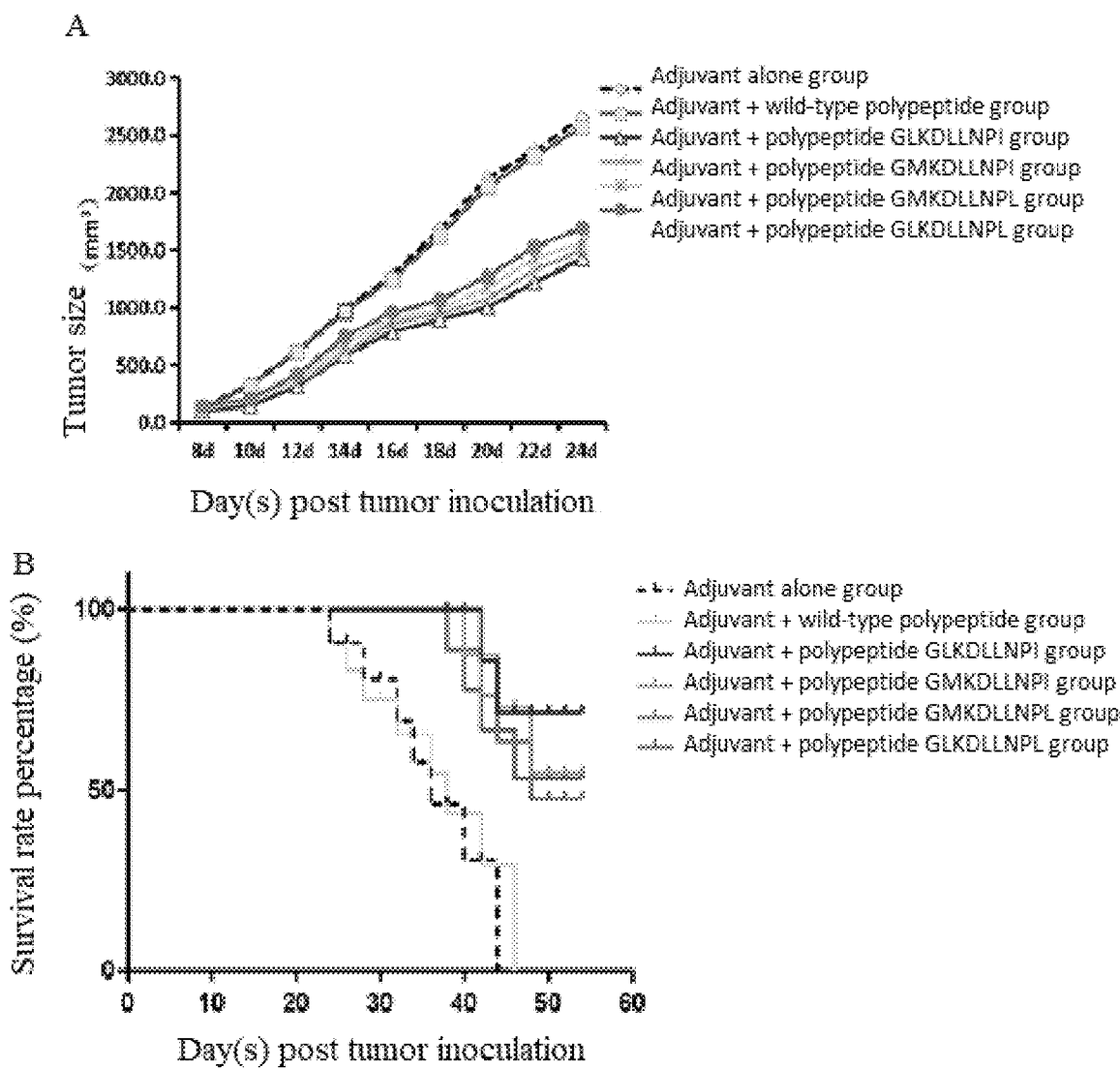
FIG. 5 is a graph showing the results of immunotherapy with the polypeptide according to an embodiment of the present disclosure.

The results are shown in FIG. 5. It can be seen, the adjuvant+mutant polypeptide (depicted in GLKDLLNPI, SEQ ID NO: 1) group, the adjuvant+mutant polypeptide's variant (depicted in GLKDLLNPL, SEQ ID NO:2) group, the adjuvant+mutant polypeptide's variant (depicted in GMKDLLNPL, SEQ ID NO:3) group and the adjuvant+mutant polypeptide's variant (depicted in GMKDLLNPI, SEQ ID NO:4) group are all capable of inhibiting tumor growth and prolonging mouse survival period effectively, compared to the adjuvant alone group and the adjuvant+wild-type polypeptide (depicted in GLEDLLNPI, SEQ ID NO: 5) group.

Example 8 Preparation of DC Polypeptide Vaccine and Therapeutic Regimen

Peripheral blood mononuclear cells (PBMCs) in 100 to 150 mL anticoagulant peripheral blood obtained from a healthy volunteer were isolated with Ficoll solution. The collected PBMCs suspended in the RPMI 1640 medium in a concentration of $2 \times 10^6$-$3 \times 10^6$ cells/ml were incubated at 37° C. for 2 hours, obtaining adherent monocytes which can be induced into DCs, and non-adherent peripheral blood lymphocytes (PBLs) for use. Such the monocytes were induced into immature DCs in the presence of GM-CSF (1000 U/ml) and IL-4 (1000 U/ml), followed by inducing to mature DCs in the presence of IFN-γ (100 U/ml) and LPS (10 ng/ml), as well as the subsequently added 10 μg/ml wild-type polypeptide (depicted in GLEDLLNPI, SEQ ID NO: 5), 10 µg/ml mutant polypeptide (depicted in GLKDLLNPI, SEQ ID NO: 1), 10 µg/ml mutant polypeptide's variant (depicted in GLKDLLNPL, SEQ ID NO:2), 10 µg/ml mutant polypeptide's variant (depicted in GMKDLLNPL, SEQ ID NO:3) and 10 µg/ml mutant polypeptide's variant (depicted in GMKDLLNPI, SEQ ID NO:4), respectively.

The subcutaneous tumor-modeled NOD/SCID mice obtained in 6.4 of the example were randomly divided into five groups as below, with 6 mice per group:

DCs loaded with the wild-type polypeptide (depicted in GLEDLLNPI, SEQ ID NO: 5) group, DCs loaded with the mutant polypeptide (depicted in GLKDLLNPI, SEQ ID NO: 1) group, DCs loaded with the mutant polypeptide's variant (depicted in GLKDLLNPL, SEQ ID NO: 2) group, DCs loaded with the mutant polypeptide's variant (depicted in GMKDLLNPL, SEQ ID NO: 3) group, and DCs loaded with the mutant polypeptide's variant (depicted in GMKDLLNPI, SEQ ID NO: 4) group.

For each of the above five groups, DCs (respectively loaded with the wild-type polypeptide, the mutant polypeptide or each of three mutant polypeptide's variants) were washed with physiological saline three times and then diluted with the physiological saline to a concentration of $(4.0\pm0.5)\times10^7$ cells/ml, and 0.1 ml of the resulting diluent (in a dosage of $(4.0\pm0.5)\times10^6$ cells) was administrated to each inner thigh close to the inguen of each mouse by intracutaneous injection, at one week interval for 2 injections in total. The vital signs of the mice were observed after administration, and the major axis (a) and the minor axis (b) of a tumor were measured by a vernier caliper every 2 days for calculation of tumor size according to a formula of a×b×b/2, with the weight change and survival rate observed and recorded.

Figure 6:
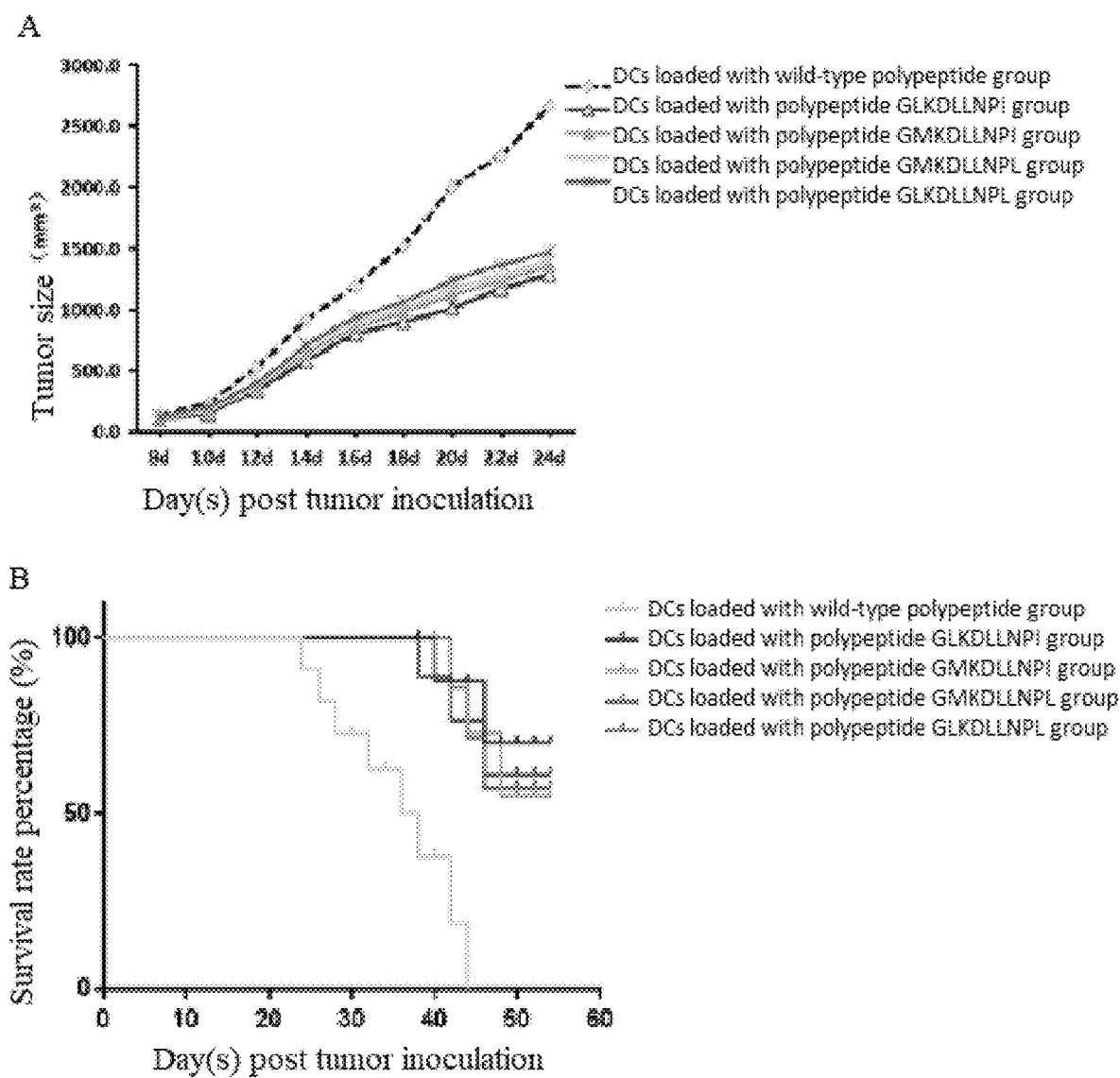
FIG. 6 is a graph showing the results of immunotherapy with the polypeptide according to an embodiment of the present disclosure, where panel A shows inhibition of tumor growth after treatment of dendritic cells (DCs) loaded with the wild-type polypeptide (depicted in GLEDLLNPI, SEQ ID NO: 5) group, DCs loaded with the mutation polypeptide (depicted in GLKDLLNPI, SEQ ID NO:1) group, DCs loaded with the mutant polypeptide's variant (depicted in GLKDLLNPL, SEQ ID NO:2) group, DCs loaded with the mutant polypeptide's variant (depicted in GMKDLLNPL, SEQ ID NO:3) group and DCs loaded with the mutant polypeptide's variant (depicted in GMKDLLNPI, SEQ ID NO:4) group respectively, and panel B shows a mouse survival rate after treatment of DCs loaded with the wild-type polypeptide (depicted in GLEDLLNPI, SEQ ID NO: 5) group, DCs loaded with the mutation polypeptide (depicted in GLKDLLNPI, SEQ ID NO:1) group, DCs loaded with the mutant polypeptide's variant (depicted in GLKDLLNPL, SEQ ID NO:2) group, DCs loaded with the mutant polypeptide's variant (depicted in GMKDLLNPL, SEQ ID NO:3) group and DCs loaded with the mutant polypeptide's variant (depicted in GMKDLLNPI, SEQ ID NO:4) group respectively.

The results are shown in FIG. 6. It can be seen, the DCs loaded with the mutant polypeptide (depicted in GLKDLLNPI, SEQ ID NO: 1) group, the DCs loaded with the mutant polypeptide's variant (depicted in GLKDLLNPL, SEQ ID NO:2) group, the DCs loaded with the mutant polypeptide's variant (depicted in GMKDLLNPL, SEQ ID NO:3) group and the DCs loaded with the mutant polypeptide's variant (depicted in GMKDLLNPI, SEQ ID NO:4) group, are all capable of prolonging the mouse survival period and mitigating tumor growth significantly, compared to the DCs loaded with the wild-type polypeptide (depicted in GLEDLLNPI, SEQ ID NO: 5) group.

Example 9 Preparation of Lentivirus-Infected DCs Vaccine and Therapeutic Regimen Peripheral blood mononuclear cells (PBMCs) in 100 to 150 mL anticoagulant peripheral blood obtained from a healthy volunteer were isolated with Ficoll solution. After the collected PBMCs were incubated at 37° C. for 2 hours and the non-adherent PBLs were removed, the adherent monocytes were cultured in the presence of recombinant human granulocyte macrophage colony stimulating factor (rhGM-CSF) and recombinant human interleukin-4 (rhIL-4). At Day 5, the medium was changed with appropriate fresh medium where cell density was adjusted to a concentration of $1\times10^6$ cells/ml, to which the lentivirus expressing the wild-type polypeptide (depicted in GLEDLLNPI, SEQ ID NO: 5), the lentivirus expressing the mutant polypeptide (depicted in GLKDLLNPI, SEQ ID NO: 1), the lentiviral expressing a mutant polypeptide's variant (depicted in GLKDLLNPL, SEQ ID NO: 2), the lentiviral expressing a mutant polypeptide's variant (depicted in GMKDLLNPL, SEQ ID NO: 3) or the lentiviral expressing a mutant polypeptide's variant (depicted in GMKDLLNPI, SEQ ID NO: 4) added respectively. After 24 hours' incubation, the collected cells with lentivirus-containing medium removed were again incubated in a fresh medium containing 50 ng/ml rhIL-4, 100 ng/ml rh GM-CSF, 100 U/ml IFN-γ and 100 ng/ml LPS in an incubator under 37° C. and 5% $CO_2$ for 48 to 72 hours, so as to induce mature DCs, and then the DCs infected with lentivirus were observed under the fluorescence microscope. The collected mature DCs were washed with physiological saline three times and diluted with the physiological saline to a concentration of $(4.0\pm0.5)\times10^7$ cells/ml for use. The subcutaneous tumor-modeled NOD/SCID mice obtained in 6.4 of the example 6 were randomly divided into five groups as below, with 6 mice per group:

DCs infected with the lentivirus expressing the wild-type polypeptide (depicted in GLEDLLNPI, SEQ ID NO: 5) group, DCs infected with the lentivirus expressing the mutant polypeptide (depicted in GLKDLLNPI, SEQ ID NO: 1) group, DCs infected with the lentivirus expressing a mutant polypeptide's variant (depicted in GLKDLLNPL, SEQ ID NO: 2) group, DCs infected with the lentiviral expressing a mutant polypeptide's variant (depicted in GMKDLLNPL, SEQ ID NO: 3) group, and DCs infected with the lentiviral expressing a mutant polypeptide's variant (depicted in GMKDLLNPI, SEQ ID NO: 4) group.

For each of the above five groups, the collected DCs (respectively infected with the lentivirus expressing the wild-type polypeptide (depicted in GLEDLLNPI, SEQ ID NO: 5), the mutant polypeptide (depicted in GLKDLLNPI, SEQ ID NO: 1), the mutant polypeptide's variant (depicted in GLKDLLNPL, SEQ ID NO:2), the mutant polypeptide's variant (depicted in GMKDLLNPL, SEQ ID NO:3) or the mutant polypeptide's variant (depicted in GMKDLLNPI, SEQ ID NO:4)) were washed with physiological saline three times and then diluted with the physiological saline to a concentration of $(4.0\pm0.5)\times10^7$ cells/ml, and 0.1 ml of the resulting diluent (in a dosage of $(4.0\pm0.5)\times10^6$ cells) was administrated to each inner thighs close to the inguen of each mouse by intracutaneous injection, at one week interval for 2 injections in total. The vital signs of the mice were observed after administration, and the major axis (a) and the minor axis (b) of a tumor were measured by a vernier caliper every 2 days for calculation of tumor size according to a formula of a×b×b/2, with the weight change and survival rate observed and recorded.

Figure 7:
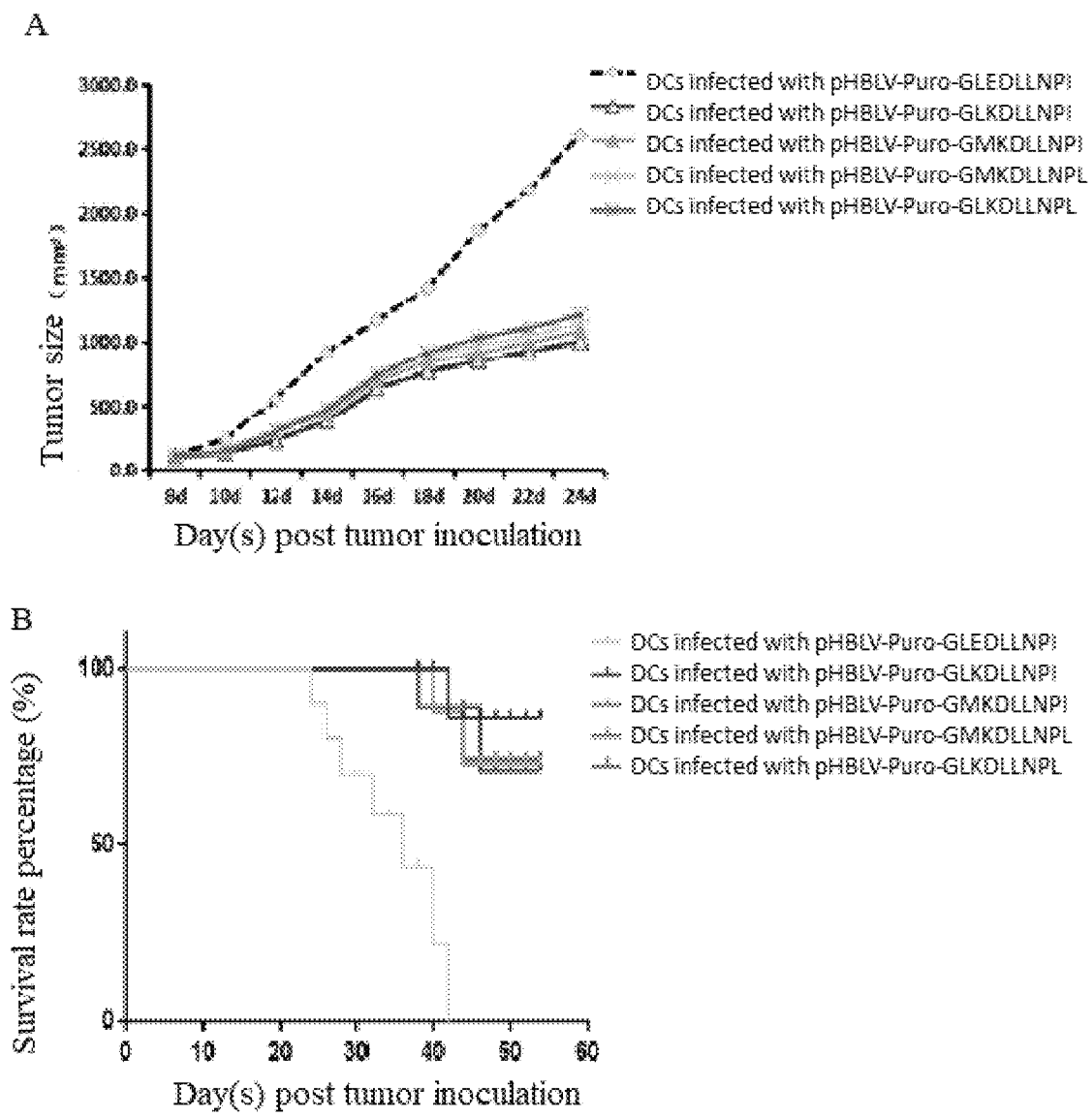
FIG. 7 is a graph showing the results of immunotherapy with the polypeptide according to an embodiment of the present disclosure, where panel A shows inhibition of tumor growth after immunotherapy with DCs infected with a lentiviral vector containing a nucleic acid sequence encoding the wild-type polypeptide (depicted in GLEDLLNPI, SEQ ID NO: 5), a lentiviral vector containing a nucleic acid sequence encoding the mutant polypeptide (depicted in GLKDLLNPI, SEQ ID NO:1), a lentiviral vector containing a nucleic acid sequence encoding a mutant polypeptide's variant (depicted in GLKDLLNPL, SEQ ID NO:2), a lentiviral vector containing a nucleic acid sequence encoding a mutant polypeptide's variant (depicted in GMKDLLNPL, SEQ ID NO:3) and a lentiviral vector containing a nucleic acid sequence encoding a mutant polypeptide's variant (depicted in GMKDLLNPI, SEQ ID NO:4), respectively, and panel B shows a mouse survival rate after immunotherapy with DCs infected with a lentiviral vector containing a nucleic acid sequence encoding the wild-type polypeptide (depicted in GLEDLLNPI, SEQ ID NO: 5), a lentiviral vector containing a nucleic acid sequence encoding the mutant polypeptide (depicted in GLKDLLNPI, SEQ ID NO:1), a lentiviral vector containing a nucleic acid sequence encoding a mutant polypeptide's variant (depicted in GLKDLLNPL, SEQ ID NO:2), a lentiviral vector containing a nucleic acid sequence encoding a mutant polypeptide's variant (depicted in GMKDLLNPL, SEQ ID NO:3) and a lentiviral vector containing a nucleic acid sequence encoding a mutant polypeptide's variant (depicted in GMKDLLNPI, SEQ ID NO:4), respectively.

The results are shown in FIG. 7. It can be seen, the DCs infected with the lentivirus expressing the mutant polypeptide (depicted in GLKDLLNPI, SEQ ID NO: 1) group, the DCs infected with the lentivirus expressing the mutant polypeptide's variant (depicted in GLKDLLNPL, SEQ ID NO:2) group, the DCs infected with the lentiviral expressing the mutant polypeptide's variant (depicted in GMKDLLNPL, SEQ ID NO:3) group and the DCs infected with the lentiviral expressing the mutant polypeptide's variant (depicted in GMKDLLNPI, SEQ ID NO:4) group are all capable of inhibiting tumor growth and prolonging mouse survival period effectively, compared to the DCs infected with the lentivirus expressing the wild-type polypeptide (depicted in GLEDLLNPI, SEQ ID NO: 5) group.

Example 10 Preparation of Polypeptide-Specific DC-CTL Vaccine and Therapeutic Regimen The CD8+ T cells sorted with CD8 magnetic beads from PBLs in the example 8 were firstly stimulated by incubating with the DCs loaded with the wild-type polypeptide (depicted in GLEDLLNPI, SEQ ID NO: 5), the DCs loaded with the mutant polypeptide (depicted in GLKDLLNPI, SEQ ID NO: 1), the DCs loaded with the mutant polypeptide's variant (depicted in GLKDLLNPL, SEQ ID NO:2), the DCs loaded with the mutant polypeptide's variant (depicted in GMKDLLNPI, SEQ ID NO:3) and the DCs loaded with the mutant polypeptide's variant (depicted in GMKDLLNPI, SEQ ID NO:4) respectively, in a ratio of 1:10 of DCs:CD8+ T cell, in an incubator under 37° C. and 5% $CO_2$ in the presence of 500 IU/ml IL-2 and 50 ng/ml IL-7, with the second and third stimulations at week 2 and week 3 using DCs loaded with corresponding polypeptides and 500 IU/ml IL-2, respectively. The number of T lymphocytes was counted at day 0, 7, 14 and 21 post incubation, for calculation of cell proliferation index (PI), where PI=cell number after proliferation/cell number seeded. The cytotoxic T lymphocytes (CTLs) were harvested at day 7 post the third stimulation, which were suspended in 0.2 ml physiological saline, and then injected intravenously to the subcutaneous tumor-modeled NOD/SCID mice via the tail in an amount of $1 \times 10^8$ cells/mouse. The vital signs of the mice were observed after administration, and the major axis (a) and the minor axis (b) of a tumor were measured by a vernier caliper every 2 days for calculation of tumor size.

Figure 8:
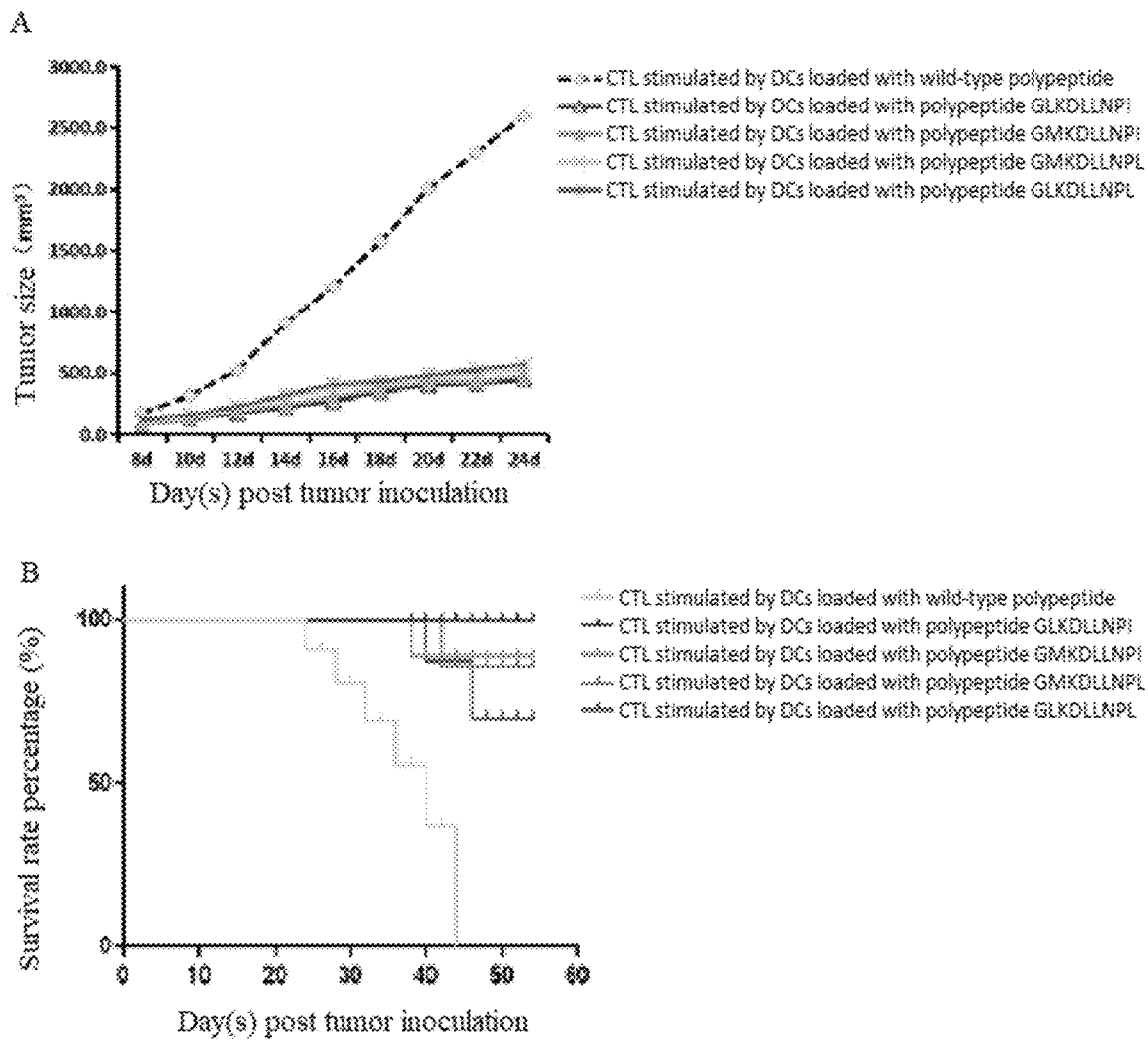
FIG. 8 is a graph showing the results of immunotherapy with the polypeptide according to an embodiment of the present disclosure, where panel A shows inhibition of tumor growth after treatment of CTLs stimulated by the DCs loaded with the wild-type polypeptide (depicted in GLEDLLNPI SEQ ID NO: 5) group, CTLs stimulated by the DCs loaded with the mutant polypeptide (depicted in GLKDLLNPI, SEQ ID NO: 1) group, CTLs stimulated by the DCs loaded with the mutant polypeptide's variant (depicted in GLKDLLNPL, SEQ ID NO:2) group, CTLs stimulated by the DCs loaded with the mutant polypeptide's variant (depicted in GMKDLLNPL, SEQ ID NO:3) group and CTLs stimulated by the DCs loaded with the mutant polypeptide's variant (depicted in GMKDLLNPI, SEQ ID NO:4) group as a vaccine, respectively; and panel B shows a mouse survival rate after treatment of CTLs stimulated by the DCs loaded with the wild-type polypeptide (depicted in GLEDLLNPI SEQ ID NO: 5) group, CTLs stimulated by the DCs loaded with the mutant polypeptide (depicted in GLKDLLNPI, SEQ ID NO: 1) group, CTLs stimulated by the DCs loaded with the mutant polypeptide's variant (depicted in GLKDLLNPL, SEQ ID NO:2) group, CTLs stimulated by the DCs loaded with the mutant polypeptide's variant (depicted in GMKDLLNPL, SEQ ID NO:3) group and CTLs stimulated by the DCs loaded with the mutant polypeptide's variant (depicted in GMKDLLNPI, SEQ ID NO:4) group as a vaccine, respectively.

The results are shown in FIG. 8. It can be seen, CTLs stimulated by the DCs loaded with the mutant polypeptide (depicted in GLKDLLNPI, SEQ ID NO: 1) group, CTLs stimulated by the DCs loaded with the mutant polypeptide's variant (depicted in GLKDLLNPL, SEQ ID NO:2) group, CTLs stimulated by the DCs loaded with the mutant polypeptide's variant (depicted in GMKDLLNPL, SEQ ID NO:3) group and CTLs stimulated by the DCs loaded with the mutant polypeptide's variant (depicted in GMKDLLNPI, SEQ ID NO:4) group as a vaccine are all capable of inhibiting tumor growth and prolonging mouse survival period significantly, compared to the CTLs stimulated by DCs loaded with the wild-type polypeptide (depicted in GLEDLLNPI SEQ ID NO: 5) group.

INDUSTRIAL APPLICABILITY

The polypeptide of the present disclosure can be used in the preparation of a kit, a medicament or a vaccine, where such the medicament or vaccine prepared has higher specificity of the immune response compared to other polypeptide vaccines against tumor, with improved safety and lower side effect (i.e. rarely causing a severe adverse response); further the polypeptide is easily to be artificially synthesized due to its simple structure, thus can be prepared as a vaccine or pharmaceutical composition against tumor.

Although embodiments of the present disclosure have been described in detail, it will be understood by those skilled in the art that various changes, modifications, substitutions and variations to the details can be made in these embodiments in accordance with the teachings of the present disclosure, which are all within the scope of the present disclosure, and the scope of the disclosure is defined by the claims and their equivalents.

In the specification of the present disclosure, the terms "an embodiment", "some embodiments", "an example", "a specific example", "some examples" or "a particular embodiment" and the like are intended to refer to particular features, structures, materials or characteristics described by way of example or embodiment are contained in at least one embodiment or example of the disclosure. In this specification, the schematic representation of the above terms does not necessarily refer to the same embodiment or example. Moreover, the particular features, structures, materials or characteristics described may be combined in any suitable manner in one or more of embodiments or examples.

What is claimed is:

1. An isolated polypeptide consisting of 9 amino acids which has at least one of amino acid substitution with Methionine at position 2 and amino acid substitution with Leucine at position 9 in the amino acid sequence as depicted in SEQ ID NO: 1 (GLKDLLNPI), and the amino acids of the isolated polypeptide at positions 1 and 3-8 are same as that of SEQ ID NO: 1.

2. The isolated polypeptide according to claim 1, wherein the isolated polypeptide is capable of binding with high affinity to HLA-A0201.

3. An isolated nucleic acid encoding the isolated polypeptide as defined in claim 1, or a complement thereof.

4. A vaccine, comprising the isolated polypeptide of claim 1 as an active pharmaceutical ingredient, and a pharmaceutically acceptable adjuvant for use in the treatment of a tumor in a HLA-A0201 positive subject.

5. The vaccine of claim 4, wherein the vaccine further comprises dendritic cells (DCs) that have been incubated with the isolated polypeptide.

6. A vaccine, comprising the isolated nucleic acid of claim 3 as an active pharmaceutical ingredient, and a carrier for use in the treatment of a tumor in a HLA-A0201 positive subject.

7. A method of treating a tumor associated with a mutation in PIK3CA gene in a HLA-A0201 positive subject in need thereof, the method comprises:
   administering to the subject a therapeutically effective amount of the vaccine of claim 4.

8. The method according to claim 7, wherein the tumor is selected from breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor.

9. A method of treating a tumor associated with a mutation in PIK3CA gene in a HLA-A0201 positive subject in need thereof, the method comprises:
   administering to the subject a therapeutically effective amount of the vaccine of claim 6.

10. The method according to claim 9, wherein the tumor is selected from breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor.

11. A diagnostic method, comprising:
   detecting whether a biological sample derived from the subject contains the isolated polypeptide as defined in claim 1, and
   determining whether the subject suffers from a tumor based on the presence or absence of the polypeptide in the biological sample.

12. The method according to claim 11, wherein the subject is an HLA-A0201 positive subject.

13. The method according to claim 12, wherein the tumor is one or more selected from the group consisting of breast cancer, lung cancer, nasopharyngeal carcinoma, liver cancer, gastric cancer, esophageal cancer, colorectal cancer, pancreatic cancer, melanoma, skin cancer, prostate cancer, cervical cancer, leukemia and brain tumor.

14. The isolated polypeptide according to claim 1, wherein the isolated polypeptide has 9 amino acids as depicted in any one of SEQ ID NO:2, SEQ ID NO:3 and SEQ ID NO:4.

\* \* \* \* \*

SEQUENCE LISTING

```
<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: Amino acid sequence of mutant polypeptide

<400> SEQUENCE: 1

Gly Leu Lys Asp Leu Leu Asn Pro Ile
1               5

<210> SEQ ID NO 2
<211> LENGTH: 9
<212> TYPE: PRT
<213> ORGANISM: Artificial Sequence
<220> FEATURE:
<223> OTHER INFORMATION: Amino acid sequence of variant 1 of mutant
      polypeptide

<400> SEQUENCE: 2

Gly Leu Lys Asp Leu Leu Asn Pro Leu
1               5
```

<210> SEQ ID NO 3
<211> LENGTH: 9
<212> TYPE: PRT
<213> ORGANISM: Artificial Sequence
<220> FEATURE:
<223> OTHER INFORMATION: Amino acid sequence of variant 2 of mutant
      polypeptide

<400> SEQUENCE: 3

Gly Met Lys Asp Leu Leu Asn Pro Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Amino acid sequence of variant 3 of mutant
      polypeptide

<400> SEQUENCE: 4

Gly Met Lys Asp Leu Leu Asn Pro Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Amino acid sequence of wild-type polypeptide

<400> SEQUENCE: 5

Gly Leu Glu Asp Leu Leu Asn Pro Ile
1               5

<210> SEQ ID NO 6
<211> LENGTH: 9
<212> TYPE: PRT
<213> ORGANISM: Artificial Sequence
<220> FEATURE:
<223> OTHER INFORMATION: Amino acid sequence of CMV polypeptide

<400> SEQUENCE: 6

Asn Leu Val Pro Met Val Ala Thr Val
1               5

<210> SEQ ID NO 7
<211> LENGTH: 27
<212> TYPE: DNA
<213> ORGANISM: Artificial Sequence
<220> FEATURE:
<223> OTHER INFORMATION: DNA sequence of nucleic acid encoding mutant
      polypeptide

<400> SEQUENCE: 7
atggattaga agatttgctg aacccta                                       27

<210> SEQ ID NO 8
<211> LENGTH: 27
<212> TYPE: DNA
<213> ORGANISM: Artificial Sequence
<220> FEATURE:
<223> OTHER INFORMATION: DNA sequence of nucleic acid encoding variant 1
      of mutant polypeptide

<400> SEQUENCE: 8
atggattaga agatttgctg aaccttA                                       27

```
<210> SEQ ID NO 9
<211> LENGTH: 25
<212> TYPE: DNA
<213> ORGANISM: Artificial Sequence
<220> FEATURE:
<223> OTHER INFORMATION: DNA sequence of nucleic acid encoding variant 2
      of mutant polypeptide

<400> SEQUENCE: 9
atgatgtaga agatttgctg aacct                                            25

<210> SEQ ID NO 10
<211> LENGTH: 27
<212> TYPE: DNA
<213> ORGANISM: Artificial Sequence
<220> FEATURE:
<223> OTHER INFORMATION: DNA sequence of nucleic acid encoding variant 3
      of mutant polypeptide

<400> SEQUENCE: 10
atggattaga agatttgctg aaccgta                                          27

<210> SEQ ID NO 11
<211> LENGTH: 27
<212> TYPE: DNA
<213> ORGANISM: Artificial Sequence
<220> FEATURE:
<223> OTHER INFORMATION: DNA sequence of nucleic acid encoding wild-type
      polypeptide

<400> SEQUENCE: 11
atggatgaaa agatttgctg aacccta                                          27
```